(12) United States Patent
Hasebe et al.

(10) Patent No.: US 9,683,174 B2
(45) Date of Patent: Jun. 20, 2017

(54) COMPOUND, POLYMER, LIQUID CRYSTAL ALIGNMENT LAYER, LIQUID CRYSTAL DISPLAY DEVICE, AND OPTICALLY ANISOTROPIC MATERIAL

(71) Applicant: DIC CORPORATION, Tokyo (JP)

(72) Inventors: Hiroshi Hasebe, Kita-adachi-gun (JP); Kazunori Maruyama, Kita-adachi-gun (JP); Fumiaki Kodera, Kita-adachi-gun (JP); Kunihiko Kotani, Kita-adachi-gun (JP); Sayaka Nose, Kita-adachi-gun (JP); Yoshio Aoki, Kita-adachi-gun (JP); Tetsuo Kusumoto, Kita-adachi-gun (JP)

(73) Assignee: DIC CORPORATION, Tokyo (JP)

( * ) Notice: Subject to any disclaimer, the term of this patent is extended or adjusted under 35 U.S.C. 154(b) by 0 days.

(21) Appl. No.: 15/039,727

(22) PCT Filed: Nov. 27, 2014

(86) PCT No.: PCT/JP2014/081444
§ 371 (c)(1),
(2) Date: May 26, 2016

(87) PCT Pub. No.: WO2015/080221
PCT Pub. Date: Jun. 4, 2015

(65) Prior Publication Data
US 2016/0376507 A1    Dec. 29, 2016

(30) Foreign Application Priority Data

Nov. 29, 2013    (JP) .................................. 2013-247984

(51) Int. Cl.
*C08F 12/26* (2006.01)
*C08F 12/28* (2006.01)
(Continued)

(52) U.S. Cl.
CPC ............ *C09K 19/56* (2013.01); *C07C 255/16* (2013.01); *C08F 22/10* (2013.01); *C08F 122/30* (2013.01);
(Continued)

(58) Field of Classification Search
CPC ... G02F 1/133711; G02F 2001/133726; G02F 2001/133742; G02F 2001/133738; C09K 19/56; C09K 19/586; C09K 19/322; C09K 19/062; C09K 2019/448; C09K 2019/2035; C07C 255/16; C08F 122/30; C08F 2222/102
(Continued)

(56) References Cited

U.S. PATENT DOCUMENTS

| 5,447,662 A | 9/1995 | Herr et al. |
| 6,335,409 B1 * | 1/2002 | Herr ........................ C07C 69/92 526/319 |

(Continued)

FOREIGN PATENT DOCUMENTS

| JP | 4-303827 A | 10/1992 |
| JP | 5-232473 A | 9/1993 |

(Continued)

OTHER PUBLICATIONS

International search report dated Feb. 24, 2015, issued in counterpart of International application No. PCT/JP2014/081444(2 pages).

*Primary Examiner* — William Cheung
(74) *Attorney, Agent, or Firm* — Westerman, Hattori, Daniels & Adrian, LLP

(57) ABSTRACT

[Object]
To provide a liquid crystal alignment layer that can easily be formed, to which an anchoring force can be efficiently induced with less polarized light for exposure, and that is effective in controlling the orientation and pretilt angle of liquid crystal molecules, and a compound and polymer that can be used for such a liquid crystal alignment layer.
[Solution]
A compound is represented by general formula (I):

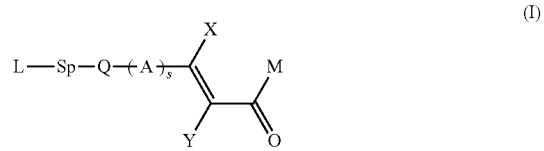

where
L is a polymerizable group;
Sp is a spacer unit containing methylene;
Q is a direct bond, —O—, or other group;
A contains a group selected from the group consisting of trans-1,4-cyclohexylene and other groups;
s is an integer of 1 to 4, where if s is 2 to 4, each A may be the same or different;
X and Y are each independently hydrogen or other group; and
M is any of general formulas (IIa), (IIb), and (IIc):

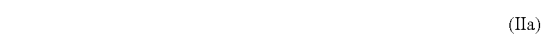
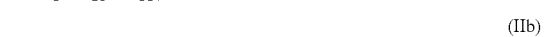
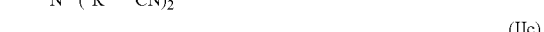

15 Claims, No Drawings

(51) Int. Cl.
  *C08F 12/24* (2006.01)
  *C09K 19/56* (2006.01)
  *G02F 1/1337* (2006.01)
  *C08F 22/10* (2006.01)
  *C08F 222/10* (2006.01)
  *C07C 255/16* (2006.01)
  *C08F 122/30* (2006.01)
  *C09K 19/32* (2006.01)
  *C09K 19/06* (2006.01)
  *C09K 19/04* (2006.01)
  *C09K 19/20* (2006.01)

(52) U.S. Cl.
  CPC ...... C08F 222/1006 (2013.01); C09K 19/062 (2013.01); C09K 19/322 (2013.01); G02F 1/133711 (2013.01); *C08F 2222/102* (2013.01); *C09K 2019/0448* (2013.01); *C09K 2019/2035* (2013.01); *G02F 2001/133738* (2013.01); *G02F 2001/133742* (2013.01)

(58) Field of Classification Search
  USPC .......................................... 526/299, 310, 313
  See application file for complete search history.

(56) References Cited

U.S. PATENT DOCUMENTS

| | | |
|---|---|---|
| 6,676,851 B1 | 1/2004 | Buchecker et al. |
| 2006/0054859 A1 | 3/2006 | Shundo et al. |
| 2010/0044632 A1 | 2/2010 | Sahade |

FOREIGN PATENT DOCUMENTS

| | | |
|---|---|---|
| JP | 6-287453 A | 10/1994 |
| JP | 7-20513 A | 1/1995 |
| JP | 9-118717 A | 5/1997 |
| JP | 2682771 B2 | 11/1997 |
| JP | 2002-517605 A | 6/2002 |
| JP | 2002-537280 A | 11/2002 |
| JP | 2003-133073 A | 5/2003 |
| JP | 2003-149647 A | 5/2003 |
| JP | 2005-206579 A | 8/2005 |
| WO | 2008/026482 A1 | 3/2008 |
| WO | 2008/044536 A1 | 4/2008 |

* cited by examiner

COMPOUND, POLYMER, LIQUID CRYSTAL ALIGNMENT LAYER, LIQUID CRYSTAL DISPLAY DEVICE, AND OPTICALLY ANISOTROPIC MATERIAL

This application is a National Stage Entry of International Application No. PCT/JP2014/065039, filed Nov. 29, 2013, which is incorporated herein by reference in its entirety.

This application is a National Stage Entry of International Application No. PCT/JP2014/081444 filed on Nov. 27, 2014, claiming a foreign priority of Japanese Patent Application No. 2013-247984 filed on Nov. 29, 2013, which is incorporated herein by reference in its entirety.

TECHNICAL FIELD

The present invention relates to compounds, polymers, liquid crystal alignment layers, liquid crystal display devices, and optically anisotropic materials. More specifically, the invention relates to liquid crystal display devices, liquid crystal alignment layers for liquid crystal display devices, compounds and polymers for the manufacture of liquid crystal alignment layers, liquid crystal display devices, and optically anisotropic materials useful as optically anisotropic films for applications such as optical compensation of liquid crystal display devices.

BACKGROUND ART

Liquid crystal alignment layers, which are intended to align liquid crystal molecules, are important for maintaining an orderly arrangement of liquid crystal molecules and thereby achieving optical characteristics based on the refractive index anisotropy of the liquid crystal molecules, thus serving as essential components of liquid crystal display devices. Since the display characteristics of liquid crystal display devices are greatly affected by the alignment of liquid crystal molecules, research has been conducted on various modes of alignment, which can generally be divided into two types: vertical alignment and horizontal alignment.

Liquid crystal display devices including vertically aligned liquid crystal layers (also referred to as "VA mode liquid crystal display device") are widely used in displays because of their superior display characteristics, including high contrast. These liquid crystal display devices, however, have insufficient viewing-angle characteristics, and various techniques for improving the viewing-angle characteristics have been researched. One common technique for improving the viewing-angle characteristics is multi-domain vertical alignment (MVA), which divides each pixel into a plurality of liquid crystal domains with different orientations (i.e., forms a multi-domain structure).

To form a multi-domain structure for MVA, it is necessary to control the tilt orientation of liquid crystal molecules. One technique that has been used is to provide slits (openings) or ribs (protrusions) on electrodes. However, the use of slits or ribs have several problems. Unlike alignment layers used for tilt orientation control in the conventional twisted nematic (TN) mode, slits and ribs are linear and may thus have uneven anchoring force on liquid crystal molecules within the pixels. This results in a distribution of response rates. Slits and ribs also decrease the light transmittance of the regions where they are provided. This results in decreased display brightness.

Another technique for controlling the tilt orientation is polymer-sustained alignment (PSA) technology, which fixes the tilt orientation of liquid crystal molecules by polymerizing a photopolymerizable or thermally polymerizable monomer added to the liquid crystal in advance while applying a voltage to tilt the liquid crystal molecules (see PTL 1). This technique could solve the problems associated with the use of slits or ribs, i.e., a distribution of response rates and decreased light transmittance. This technique, however, has other problems, including variations in characteristics due to the monomer added to the liquid crystal, difficult process control, and the influence of residual monomer.

It is therefore preferred for VA mode liquid crystal display devices to have a multi-domain structure formed by tilt orientation control using alignment layers. One technique for inducing the force for controlling the tilt orientation is rubbing, which involves forming a layer such as a polyimide layer on a substrate and rubbing the layer with rubbing cloth to control the orientation and pretilt angle thereof. Rubbing, however, is not suitable for forming a fine mufti-domain structure and also has a problem in that it generates triboelectric charge and impurities.

Examples of liquid crystal display devices including horizontally aligned liquid crystal layers include IPS mode liquid crystal display devices. IPS mode liquid crystal display devices are widely used in displays because of their superior display characteristics, including low viewing angle dependence of contrast and color. IPS mode, however, requires the pretilt angle to be controlled to 1° or less on the electrode surfaces to reduce the viewing angle dependence and color reproductivity in the black state.

Rubbing is also commonly used as a technique for inducing the force for controlling the tilt orientation to achieve horizontal alignment. However, one problem arises in that the process of rubbing a polyimide layer to achieve horizontal alignment induces a pretilt angle of more than 1° to liquid crystal molecules, which makes it difficult to achieve the desired display characteristics.

As discussed above, the control of the orientation and pretilt angle of liquid crystal molecules using alignment layers is important for improving the display characteristics fox both vertical alignment and horizontal alignment.

Besides rubbing, photoalignment is known as a technique for inducing the force for controlling the tilt orientation (see PTL 2). Photoalignment facilitates the formation of fine multi-domain structures with varying light exposure patterns and also involves no contact with the layer and thus generates little or no triboeleetric charge and impurities. Photoalignment would therefore solve the foregoing problems and improve the display characteristics.

Examples of known materials that can be used to achieve alignment by photoalignment include compounds having photochemically isomerizable sites, such as azobenzene derivatives (see PTL 3); compounds having photochemically crosslinkable sites, such as cinnamic acid derivatives, coumarin derivatives, and chalcone derivatives (see PTLs 4, 5, and 6), and anisotropically photodegradable compounds such as polyimide derivatives.

CITATION LIST

Patent Literature

PTL 1: Japanese Unexamined Patent Application Publication No. 2003-149647

PTL 2: Japanese Patent No. 2682771

PTL 3: Japanese Unexamined Patent Application Publication No. 5-232473

PTL 4: Japanese Unexamined Patent Application Publication No. 6-287453

PTL 5: Japanese Unexamined Patent Application Publication No. 9-118717

PTL 6: Japanese Unexamined Patent Application Publication (Translation of PCT Application) No. 2002-517605

SUMMARY OF INVENTION

Technical Problem

An object of the present invention is to provide a liquid crystal alignment layer that can easily be formed, to which an anchoring force can be efficiently induced with less polarized light for exposure, and that is effective in controlling the orientation and pretilt angle of liquid crystal molecules, and also to provide a compound and polymer that can be used for such a liquid crystal alignment layer.

Solution to Problem

After conducting extensive research on various materials to solve the foregoing problems, the inventors have discovered that a layer containing a polymer having structural units derived from a particular compound having a cyano group at an end thereof and cured by exposure to polarized light has a sufficient anchoring force and is effective in controlling the orientation and pretilt angle of liquid crystal molecules. This discovery has led to the present invention.

Specifically, the present invention provides Items (1) to (15) below.

(1) A compound is represented by general formula (1) below.

[Chem. 1]

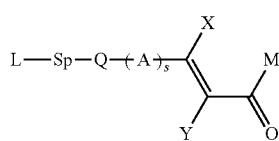

(I)

In the formula,

L is a polymerizable group;

Sp is a spacer unit containing methylene;

Q is a direct bond, —O—, —CO—O—, or —O—CO—;

A contains a group selected from the group consisting of trans-1,4-cyclohexylene (where one or more non-adjacent methylene groups present in this group are optionally replaced with —O—, —NH—, or —S—), 1,4-phenylene (where one or more —CH= groups present in this group are optionally replaced with —N=), 1,4-cyclohexenylene, 2,5-thiophenylene, 2,5-furanylene, 1,4-bicyclo[2.2.2]octylene, naphthalene, 1,4-diyl, naphthalene-2,6-diyl, decahydronaphthalene-2,6-diyl, and 1,2,3,4-tetrahydronaphthalene-2,6-diyl, where the groups are unsubstituted, or one or more hydrogen atoms present therein are optionally replaced with fluorine, chlorine, cyano, methyl, or methoxy;

s is an integer of 1 to 4, where if s is 2 to 4, each A may be the same or different;

X and Y are each independently hydrogen, fluorine, chlorine, cyano, or an alkyl group of 1 to 20 carbon atoms, where any hydrogen atom present in the alkyl group is optionally replaced with fluorine, and if one or more non-adjacent methylene groups are present in the alkyl group, the one or more non-adjacent methylene groups are optionally replaced with —O—, —CO—O—, —O—CO—, and/or —CH=CH—; and M is any of general formulas (IIa), (IIb), and (IIc) below.

[Chem. 2]

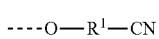 (IIa)

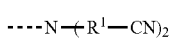 (IIb)

 (IIc)

In formulas (IIa), (IIb), and (IIc), the dashed line is a linkage to the carbon atom;

$R^1$ is an alkylene group of 1 to 30 carbon atoms, where each $R^1$, if present, may be the same or different;

$R^2$ is hydrogen or an alkyl group of 1 to 30 carbon atoms; and if one or more non-adjacent methylene groups are present in $R^1$ and $R^2$, the one or more non-adjacent methylene groups are optionally replaced with —O—, —CO—, —CO—O—, —O—CO—, —CO—NH—, —NH—CO—, —NCH$_3$—, —CH=CH—, —CF=CF—, and/or —C≡C—, and any hydrogen atom present in $R^1$ and $R^2$ is optionally replaced with an alkyl group of 1 to 20 carbon atoms, cyano, or halogen, (2) In the compound according to Item (1) above, $R^1$ in general formulas (IIa), (IIb), and (IIc) is represented by general formula (IId) below.

[Chem. 3]

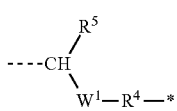 (IId)

In the formula, the dashed line is a linkage to the oxygen or nitrogen atom, and * is a linkage to the cyano. group;

$W^1$ is methylene (where any hydrogen atom present in this group is optionally replaced with an alkyl group of 1 to 5 carbon atoms), —CO—O—, or —CO—NH—;

$R^4$ is an alkylene group of 1 to 20 carbon atoms, where if one or more non-adjacent methylene groups are present in the alkylene group, the one or more non-adjacent methylene groups are optionally replaced with —O—, —CO—, —CO—O—, —O—CO—, —CO—NH—, —NH—CO—, or —NCH$_2$—; and $R^5$ is hydrogen or an alkyl group of 1 to 5 carbon atoms, where any hydrogen atom present in the alkyl group is optionally replaced with fluorine or chlorine.

(3) In the compound according to Item (1) or (2) above, A in general formula (I) is 1,4-phenylene, where one or more hydrogen atoms present in the 1,4-phenylene group are optionally replaced with fluorine, chlorine, methyl, or methoxy.

(4) In the compound according to any one Of Items (1) to (3) above, X and Y in general formula (I) are hydrogen.

(5) In the compound according to any one of Items (1) to (4) above, L in general formula (I) is any polymerizable group selected from the group consisting of polymerizable groups represented by general formulas (III-1) to (III-10) below.

[Chem. 4]

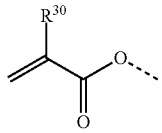
(III-1)

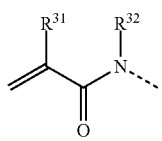
(III-2)

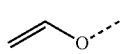
(III-3)

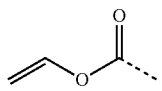
(III-4)

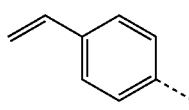
(III-5)

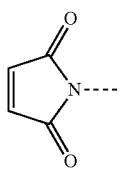
(III-6)

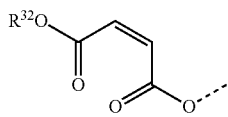
(III-7)

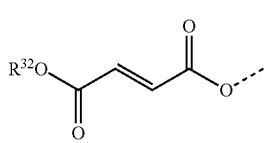
(III-8)

(III-9)

(III-10)

In the formulas, the dashed line is a linkage to Sp; $R^{30}$ is hydrogen, fluorine, chlorine, an alkyl group of 1 to 4 carbon atoms, phenyl, or phenoxy; $R^{31}$ is hydrogen, chlorine, methyl, or phenyl; and $R^{32}$ is each independently hydrogen or an alkyl group of 1 to 5 carbon atoms, (6) In the compound according to any one of Items (1) to (4) above, L in general formula (I) is any of polymerizable groups represented by general formulas (III-1), (III-2), and (III-6) below.

[Chem. 5]

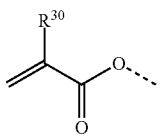
(III-1)

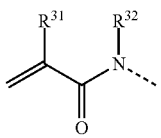
(III-2)

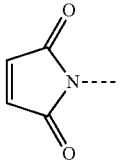
(III-6)

In the formulas, the dashed line is a linkage to Sp; $R^{30}$ and $R^{31}$ are each independently hydrogen or methyl; and $R^{32}$ is hydrogen or an alkyl group of 1 to 5 carbon atoms, (7) In the compound according to any one of Items (1) to (7) above, $-(A)_s-$ in general formula (I) is represented by general formula (IVa) below.

[Chem. 6]

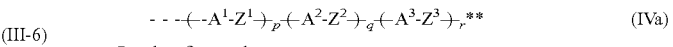
(IVa)

In the formula,
the dashed line is a linkage to Q, and ** is a linkage to the carbon atom;

$A^1$, $A^2$, and $A^3$ are each independently a group selected from the group consisting of trans-1,4-cyclohexylene (where one or more non-adjacent methylene groups present in this group are optionally replaced with —O—, —NH—, or —S—), 1,4-phenylene (where one or more —CH= groups present in this group are optionally replaced with —N=), 1,4-cyclohexenylene, 2,5-thiophenylene, 2,5-furanylene, 1,4-bicyclo[2.2.2]octylene, naphthalene-1,4-diyl, naphthalene-2,6-diyl, decahydronaphthalene-2,6-diyl, and 1,2,3,4-tetrahydronaphthalene-2,6-diyl, where the groups are unsubstituted, or one or more hydrogen atoms present therein are optionally replaced with fluorine, chlorine, cyano, methyl, or methoxy;

$Z^1$, $Z^2$, and $Z^3$ are each independently a single bond, an alkylene group of 1 to 20 carbon atoms, —OCH$_2$—, —CH$_2$O—, —COO—, —OCO—, —CH=CH—, —CF=CF—, —CF$_2$O—, —OCF$_2$—, —CF$_2$CF$_2$—, or —C≡C—, where if one or more non-adjacent methylene groups are present in these substituents, the one or more non-adjacent methylene groups are each independently optionally replaced with —O—, —CO—, —CO—O—, —O—CO—, —Si(CH$_3$)$_2$—O—Si(CH$_3$)$_2$—, —NR$^6$—, —NR$^6$—CO—, —CO—NR$^6$—, —NR$^6$—CO—O—, —O—CO—NR$^6$—, —NR$^6$—CO—NR$^6$—, —CH=CH—, —C≡C—, or —O—CO—O—, where $R^6$ is each independently hydrogen or an alkyl group of 1 to 5 carbon atoms; and p, q, and r are each an integer of 0 to 4, where p+q+r=s.

(8) In the compound according to Item (7) above, in general formula (IVa), $A^2$ is any of trans-1,4-cyclohexylene, 2,6-naphthylene, pyridine-2,5-diyl, pyrimidine-2,5-diyl, and 1,4-phenylene, where one or more hydrogen atoms present in the groups; are optionally replaced with fluorine, chlorine, methyl, or methoxy;

$Z^2$ is any of a single bond, an alkylene group of 1 to 20 carbon atoms, —OCH$_2$—, —CH$_2$O—, —CO—O—, —O—CO—, —CH=CH—, and —C≡C—, where if one or more non-adjacent methylene groups are present in the groups, the one or more non-adjacent methylene groups are each independently optionally replaced with —O—, —CO—, —CO—O—, —O—CO—, —CH=CH—, or —C≡C—; and q is 1.

(9) In the compound according to Item (7) above, $A^2$ in general formula (IVa) is 1,4-phenylene, where one or more hydrogen atoms present in the 1,4-phenylene group are optionally replaced with fluorine, chlorine, methyl, or methoxy.

(10) A polymer is obtained by polymerization of a composition containing the compound according to any one of Items (1) to (9) above. The polymer contains structural units represented by general formula (PI) below.

[Chem. 7]

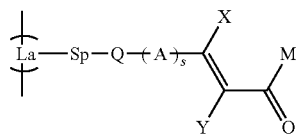

(PI)

In the formula, La is a group derived from L, and Sp, Q, A, X, Y, M, and s are as defined in general formula (I).

(11) A liquid crystal alignment layer for use in a vertically aligned liquid crystal display device contains a cured product of the polymer according to Item (10) above.

(12) A vertically aligned liquid crystal display device includes the liquid crystal alignment layer according to Item (11) above.

(13) A liquid crystal alignment layer for use in a horizontally aligned liquid crystal display device contains a cured product of the polymer according to Item (10) above.

(14) A horizontally aligned liquid crystal display device includes the liquid crystal alignment layer according to item (13) above.

(15) An optically anisotropic material is made of a polymer of a polymerizable liquid crystal composition. Polymerizable liquid crystal molecules in the polymerizable liquid crystal composition are aligned by a liquid crystal alignment layer containing a cured product of the polymer according to Item (10) above.

Advantageous Effects of Invention

The present invention can provide a liquid crystal alignment layer that can easily be formed, to which an anchoring force can be efficiently induced with less polarized light for exposure, and that is effective in controlling the orientation and pretilt angle of liquid crystal molecules and a compound and polymer that can be used for such a liquid crystal alignment layer. The present invention can also provide a liquid crystal display device including such a liquid crystal alignment layer and an optically anisotropic material.

DESCRIPTION OF EMBODIMENTS

Preferred examples of the present invention will now be described, although these examples are not intended to limit the invention. Additions, omissions, substitutions, and other modifications can be made without departing from the spirit of the invention.

A liquid crystal alignment layer according to an embodiment contains, a cured product of a polymer having structural units derived from a particular compound having a cyano group at an end of the molecule. The liquid crystal alignment layer is effective in controlling the orientation and pretilt angle of liquid crystals and can also have a higher voltage holding ratio (VHR) than conventional liquid crystal alignment layers. The voltage holding ratio (VHR) is a measure of the ability to retain a voltage applied to each pixel in a liquid crystal display device for a predetermined period of time (e.g., 16.7 msec, which is a typical frame time for liquid crystal display devices). Since the liquid crystal alignment layer according to this embodiment has a high voltage holding ratio (VHR) and is effective in controlling the orientation and pretilt angle of liquid crystals, it can be used to efficiently manufacture a liquid crystal display device and optically anisotropic material with high display quality and reliability.

The particular compound having a cyano group at an end of the molecule according to this embodiment will be described first.

The compound according to this embodiment is represented by general formula (I) below.

[Chem. 8]

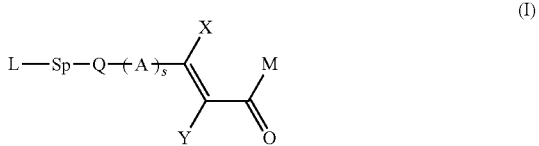

(I)

In general formula (I) above,

L is a polymerizable group;

Sp is a spacer unit containing methylene;

Q is a direct bond, —O—, —CO—O—, or —O—O—CO—;

A contains a group selected from the group consisting of trans-1,4-cyclohexylene (where one or more non-adjacent methylene groups present in this group are optionally replaced with —O—, —NH—, or —S—), 1,4-phenylene (where one or more —CH= groups present in this group are optionally replaced with —N=), 1,4-cyclohexenylene, 2,5-thiophenylene, 2,5-furanylene, 1,4-bicyclo[2.2.2]octylene, naphthalene-1,4-diyl, naphthalene-2,6-diyl, decahydronaphthalene-2,6-diyl, and 1,2,3,4-tetrahydxonaphthalene-2,6-diyl, where the groups are unsubstituted, or one or more hydrogen atoms present therein are optionally replaced with fluorine, chlorine, cyano, methyl, or methoxy;

s is an integer of 1 to 4, where if s is 2 to 4, each A may be the same or different;

X and Y are each independently hydrogen, fluorine, chlorine, cyano, or an alkyl group of 1 to 20 carbon atoms, where any hydrogen atom present in the alkyl group is optionally replaced with fluorine, and if one or more non-adjacent methylene, groups are present in the alkyl group, the one or more non-adjacent methylene groups are optionally replaced with —O—, —CO—O—, —O—CO—, and/or —CH=CH—; and M is any of general formulas (IIa), (IIb), and (IIc) below.

[Chem. 9]

----O—R$^1$—CN  (IIa)

----N—(R$^1$—CN)$_2$  (IIb)

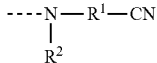  (IIc)

In general formulas (IIa), (IIb), and (IIc) above,
the dashed line is a linkage to the carbon atom;
R$^1$ is an alkylene group of 1 to 30 carbon atoms, where each R$^1$, if present, may be the same or different;
R$^2$ is hydrogen or an alkyl group of 1 to 30 carbon atoms; and
if one or more non-adjacent methylene groups are present in R$^1$ and R$^2$, the one or more non-adjacent methylene groups are optionally replaced with —O—, —CO—, —CO—O—, —O—CO—, —CO—NH—, —NH—CO—, —NCH$_3$—, —CH═CH—, —CF═CF—, and/or —C≡C—, and any hydrogen atom present in R$^1$ and R$^2$ is optionally replaced with an alkyl group of 1 to 20 carbon atoms, cyano, or halogen.

In general formulas (IIa), (IIb), and (IIc) above, the alkylene group of 1 to 30 carbon atoms represented by R$^1$ may be linear, branched, or cyclic. Any methylene group present in a linear or branched alkylene group is optionally replaced with a 3- to 8-membered cycloalkylene group. Preferably, R$^1$ is an alkylene group of 1 to 3 carbon atoms or an alkenylene group of 1 to 3 carbon atoms. In general formulas (IIa), (IIb), and (IIc) above, —R$^1$—CN is preferably any of formulas (W-1) to (W-4) below, more preferably formula (W-1) or (W-2).

[Chem. 10]

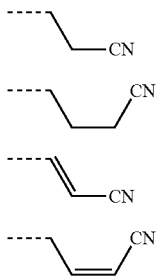

(W-1)
(W-2)
(W-3)
(W-4)

In general formulas (IIa), (IIb), and (IIc) above, the alkyl group of 1 to 30 carbon atoms represented by R$^2$ may be linear, branched, or cyclic. Any methyl group present in a linear or branched alkyl group is optionally replaced with a 3- to 8-membered cycloalkyl group. Any methylene group present in a linear or branched alkyl group is optionally replaced with a 3- to 8-membered cycloalkylene group, In general formulas (IIa), (IIb), and (IIc) above, R$^1$ is preferably a group represented by general formula (IId) below.

[Chem. 11]

  (IId)

In general formula (IId) above,
the dashed line is a linkage to the oxygen or nitrogen atom, and * is a linkage to the cyano group;
W$^1$ is methylene (where any hydrogen atom present in this group is optionally replaced with an alkyl group of 1 to 5 carbon atoms), —CO—O—, or —CO—NH—;
R$^4$ is an alkylene group of 1 to 20 carbon atoms, where if one or more non-adjacent methylene groups are present in the alkylene group, the one or more non-adjacent methylene groups are optionally replaced with —O—, —CO—, —CO—O—, —O—CO—, —CO—NH—, —NH—CO—, or —NCH$_3$—; and
R$^5$ is hydrogen or an alkyl group of 1 to 5 carbon atoms, where any hydrogen atom present in the alkyl group is optionally replaced with fluorine or chlorine.

In general formula (IIc) above, R$^2$ is preferably a linear or cyclic alkyl group of 2 to 8 carbon atoms, more preferably a linear or cyclic alkyl group of 2 to 4 carbon atoms, even more preferably a linear alkyl group of 2 to 4 carbon atoms. This further improves the anchoring force of the liquid crystal alignment layer.

R$^2$ is also preferably a linear or cyclic alkyl group of 1 to 12 carbon atoms. This improves the voltage holding ratio of the liquid crystal alignment layer.

R$^2$ is also preferably a linear or cyclic alkyl group of 1 to 6 carbon atoms. This reduces residual charge on the liquid crystal alignment layer.

In general formula (I) above, -(A)$_s$- is preferably a structure represented by general formula (IVa) below. This structure further improves the liquid crystal alignment properties of the liquid crystal alignment layer.

[Chem. 12]

----(-A$^1$-Z$^1$-)$_p$(-A$^2$-Z$^2$-)$_q$(-A$^3$-Z$^3$-)$_r$**  (IVa)

In general formula (IVa) above,
the dashed line is a linkage to Q, and ** is a linkage to the carbon atom;
A$^1$, A$^2$, and A$^3$ and are each independently a group selected from the group consisting of trans-1,4-cyclohexylene (where one or more non-adjacent methylene groups present in this group are optionally replaced with —O—, —NH—, or —S—), 1,4-phenylene (where one or more —CH═ groups present in this group are optionally replaced with —N═), 1,4-cyclohexenylene, 2,5-thiophenylene, 2,5-furanylene, 1,4-bicyclo[2.2.2]octylene, naphthalene-1,4-diyl, naphthalene-2,6-diyl, decahydronaphthalene-2,6-diyl, and 1,2,3,4-tetrahydronaphthalene-2,6-diyl, where the groups are unsubstituted, or one or more hydrogen atoms present therein are optionally replaced with fluorine, chlorine, cyano, methyl, or methoxy;
Z$^1$, Z$^2$, and Z$^3$ are each independently a single bond, an alkylene group of 1 to 20 carbon atoms, —OCH$_2$—, —CH$_2$O—, —CO—O—, —O—CO—, —CH═CH—, —CF═CF—, —CF$_2$O—, —OCF$_2$—, —CF$_2$CF$_2$—, or —C≡C—, where if one or more non-adjacent methylene groups are present in these substituents, the one or more non-adjacent methylene groups are each independently optionally replaced with —O—, —CO—, —CO—O—, —O—CO—, —Si(CH$_3$)$_2$—O—Si(CH$_3$)$_2$—, —NR$^6$—, —NR⁶—CO—, —CO—NR⁶—, —NR⁶—CO—O—, —O—CO—NR⁶—, —NR⁶—CO—NR⁶—, —CH═CH—, —C≡C—, or —O—C—, where R⁶ is each independently hydrogen or an alkyl group of 1 to 5 carbon atoms; and p, q, and r are each an integer of 0 to 4, where p+q+r=s, more preferably p+q+r=2, even more preferably r=1 and p+q=1.

In general formulas (I) and (IVa) above, A, A¹, A², and A³ are preferably pyridine-2,5-diyl, pyrimidine-2,5-diyl, 1,2,4,5-tetrazine-2,5-diyl, or 1,4-phenylene, more preferably pyrimidine-2,5-diyl. This further improves the anchoring force of the liquid crystal alignment layer and thereby improves the anchoring effect.

A, A¹, A², and A³ may also be 1,4-naphthylene, 2,6-naphthylene, 2,5-thiophenylene, or 2,5-furanylene. This further improves the solubility of the resulting polymer.

A, A¹, A², and A³ may also be pyridine-5-diyl, pyrimidine-2,5-diyl, 2,5-thiophenylene, or 1,4-phenylene. This allows the induction of an anchoring force to the liquid crystal alignment layer with even less light for exposure.

A, A¹, A², and A³ may also be pyrimidine-2,5-diyl, 2,5-thiophenylene, 2,6-naphthylene, or 2,5-furanylene. This allows the formation of the liquid crystal alignment layer by photoalignment with light of a longer wavelength.

More preferably, A, A¹, A², and A⁴ in general formulas (I) and (IVa) above are 1,4-phenylene where one or more hydrogen atoms are optionally replaced with fluorine, chlorine, methyl, or methoxy, even more preferably 1,4-phenylene where one or more hydrogen atoms are replaced with methoxy. If A, A¹, A², and A³ are such groups, the compound represented by general formula (I) above can be used to provide a composition with good coating suitability, and the resulting polymer can be cured to form a liquid crystal alignment layer with an improved anchoring force and property of controlling the pretilt angle. A liquid crystal alignment layer and a liquid crystal display device with a high voltage holding ratio can also be provided, In general formula (IVa) above, Z¹, Z², and Z³ are preferably —NR⁶—, —NR⁶—CO—, —CO—NR⁶—, —NR⁶—CO—O—, —O—CO—NR⁶—, —NR⁶—CO—NR⁶—, or —O—CO—O—. This improves the thermal stability of the liquid crystal alignment properties.

Z¹, Z², and Z³ are also preferably —OCH₂—, —CH₂O—, —CO—O—, —O—CO—, —CF₂O—, —OCF₂—, —CF₂CF₂—, or —NR⁶—. This improves the solubility of the polymer.

In the compound represented by general formula (I) above, X and Y are preferably hydrogen. If X and Y are hydrogen, a polymer obtained from the compound can be used to form a liquid crystal alignment layer with an improved voltage holding ratio, X and Y are also preferably fluorine, chlorine, or cyano. This allows the formation of the liquid crystal alignment layer by photoalignment with light of a longer wavelength.

In the compound represented by general formula (I) above, L is a polymer sizable group, which can be polymerized with each other. In general formula (I) above, L is preferably any polymerizable group selected from the group consisting of general formulas (III-1) to (III-10) below, more preferably general formula (III-1), (III-2), or (III-6), even more preferably general formula (III-1).

[Chem. 13]

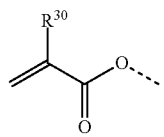
(III-1)

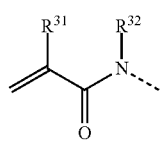
(III-2)

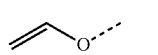
(III-3)

(III-4)

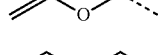
(III-5)

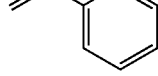
(III-6)

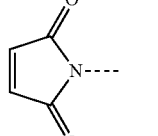
(III-7)

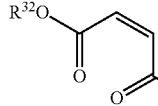
(III-8)

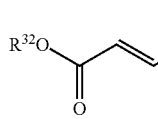
(III-9)

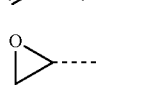
(III-10)

In general formulas (III-1) to (III-10) above, the dashed line is a linkage to Sp; R³⁰ is hydrogen, fluorine, chlorine, an alkyl group of 1 to 4 carbon atoms, phenyl, or phenoxy; R³¹ is hydrogen, chlorine, methyl, or phenyl; and R³² is independently hydrogen or an alkyl group of 1 to 5 carbon atoms. In the polymerizable groups represented by general formulas (III-1), III-2), and (III-6), R³⁰ and R³¹ are preferably each independently hydrogen or methyl.

In general formula (I) above, L is preferably a polymerizable group represented by general formula (III-1) where R³⁰ is methyl, phenyl, or phenoxy, a polymerizable group represented by general formula (III-2) where R³¹ is methyl or phenyl, or a polymerizable group represented by general formula (III-6), (III-7), (III-8), or (III-9). This further improves the stability of alignment on the liquid crystal alignment layer according to this embodiment.

L is also preferably a polymerizable group represented by general formula (III-1). This further improves the property of controlling the orientation and pretilt angle of liquid crystals and thereby improves the voltage holding ratio (VHR).

L is also preferably a polymerizable group represented by general formula (III-1) or (III-2) where $R^{30}$ or $R^{31}$ is hydrogen, chlorine, or methyl or a polymerizable group represented by general formula (III-3), (III-4), (III-7), (III-9), or (III-10), more preferably a polymerizable group represented by general formula (III-1), (III-3), (III-4), or (III-10). This improves the solubility of the resulting polymer.

L is also preferably a polymerizable group represented by general formula (III-1) or (III-2) where $R^{30}$ or $R^{31}$ is chlorine or a polymerizable group represented by general formula (III-3), (III-4), (III-6), (III-7), (III-8), (III-9), or (III-10), more preferably a polymerizable group represented by general formula (III-1), (III-2), or (III-2) where $R^{30}$ or $R^{31}$ is chlorine or a polymerizable group represented by general formula (III-3), (III-4), or (III-10). This improves the polymerization rate of the compound represented by general formula (I).

L is also preferably a polymerizable group represented by general formula (III-1). where $R^{30}$ is methyl or a polymerizable group represented by general formula (III-3), (III-4), or (III-5). This reduces the molecular weight distribution of the polymer according to this embodiment.

L is also preferably a polymerizable group represented by general formula (III-1) where $R^{30}$ is hydrogen, a polymerizable group represented by general formula (III-2) where $R^{31}$ is hydrogen, chlorine, methyl, or phenyl, or a polymerizable group represented by general formula (III-3), (III-4), (III-6), or (III-10), more preferably a polymerizable group represented by general formula (III-2) where $R^{31}$ is hydrogen, chlorine, or methyl or a polymerizable group represented by general formula (III-6). This improves the adhesion of the resulting polymer to substrates.

In general formula (I) above, Sp is a spacer containing methylene and may be an alkylene or oxyalkylene group. Preferably, Sp is an alkylene group of 1 to 20 carbon atoms or an oxyalkylene group of 1 to 20 carbon atoms, more preferably an alkylene group of 6 to 14 carbon atoms or an oxyalkylene group of 6 to 14 carbon atoms, even more preferably an alkylene group of 8 to 12 carbon atoms or an oxyalkylene group of 8 to 12 carbon atoms. Such groups can be selected for Sp to provide a liquid crystal alignment layer with a larger anchoring energy. A preferred oxyalkylene group is oxyethylene.

These alkylene and oxyalkylene groups may be linear or branched. If one or more non-adjacent methylene groups are present in the linear or branched alkylene groups, the one or more non-adjacent methylene groups are each independently optionally replaced with —O—, —CO—, —CO—O—, —O—CO—, —NR$^7$—, —NR$^7$—CO—, —CO—NR$^7$—, —NR$^7$—CO—O—, —O—CO—NR$^7$—, —NR$^7$—CO—NR$^7$—, —CH=CH—, —C≡C—, or —O—CO—O—, where $R^7$ is alkyl.

Preferred compounds represented by general formula (I) according to this embodiment are those represented by general formula (Ia) below.

[Chem. 14]

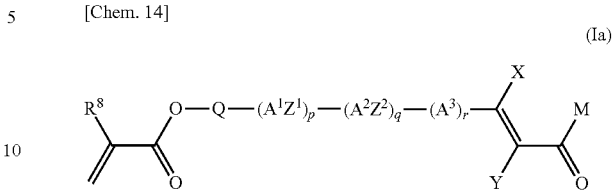

(Ia)

In general formula (Ia) above, $R^8$ is hydrogen, fluorine, chlorine, or an alkyl group of 1 to 4 carbon atoms; Q, X, Y, and M are as defined in general formula (I); and $A^1$, $A^2$, $A^3$, $Z^1$, $Z^2$, p, q, and r are as defined in general formula (IVa). Preferably, $R^8$ is hydrogen, chlorine, or methyl. More preferably, p+q+r=2, and even more preferably, r=1 and p=1 or q=1.

More preferred compounds represented by general formula (I) according to this embodiment are those represented by general formula (Ib) below.

[Chem. 15]

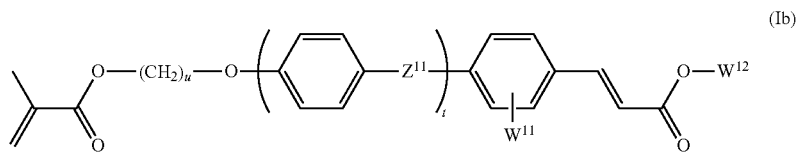

(Ib)

In general formula (Ib) above, u is an integer of 2 to 12; t is an integer of 0 or 1; $Z^{11}$ is a single bond, —COO—, or —OCO—; $W^{11}$ is hydrogen, fluorine, methyl, methoxy, ethyl, or ethoxy; and $W^{12}$ is any of general formulas ($W^{12}$-1) to ($W^{12}$-4) below.

[Chem. 16]

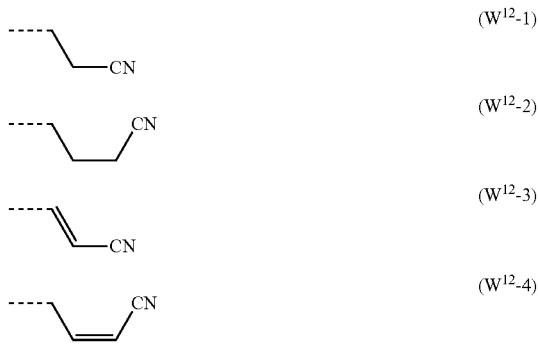

In general formula (Ib) above, $Z^{11}$ is preferably —COO—. Also preferably, u is 8 to 12, t is 1, and $W^{11}$ is methyl or methoxy, which provides good alignment with less polarized ultraviolet light for exposure. $W^{12}$ is preferably a group represented by general formula ($W^{12}$-1).

Even more preferred compounds represented by general formula (I) according to this embodiment are those represented by general formulas (I-1) to (I-57) below.

[Chem. 17]
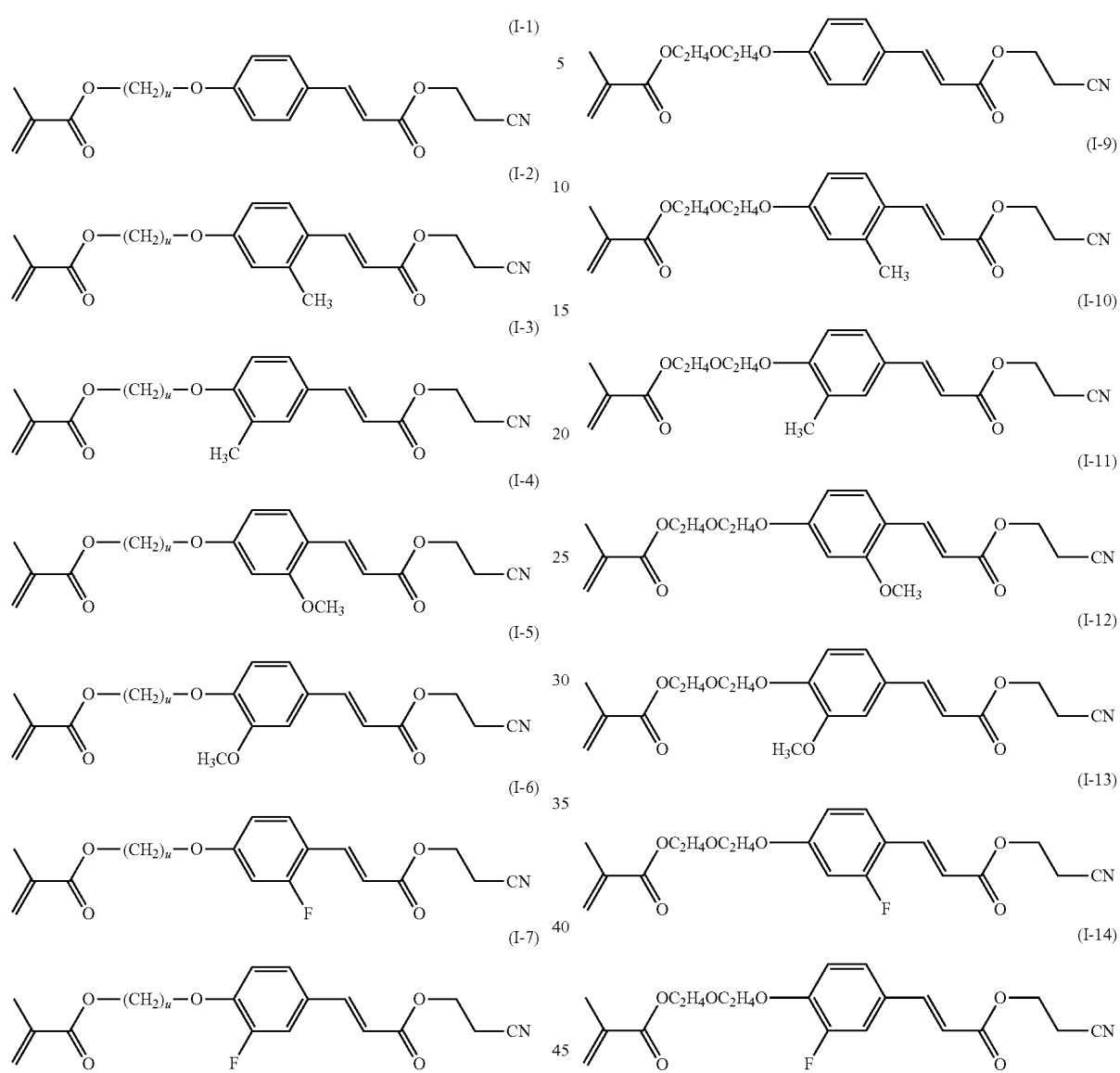
[Chem. 18]
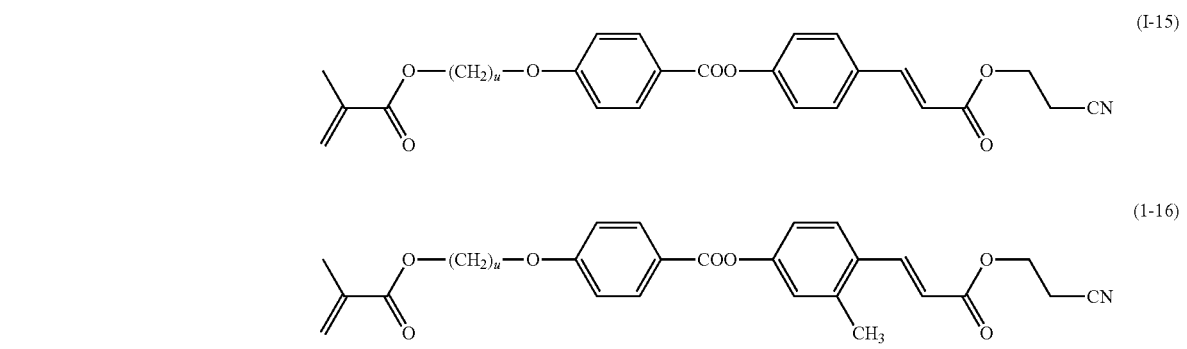

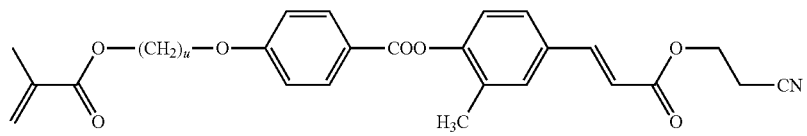
(I-17)
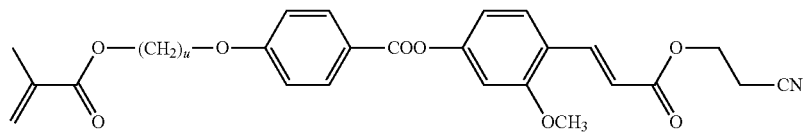
(I-18)
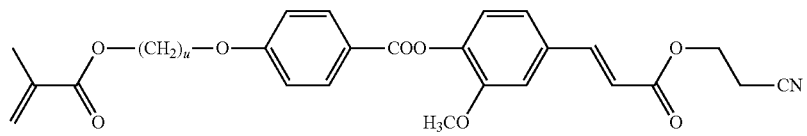
(I-19)
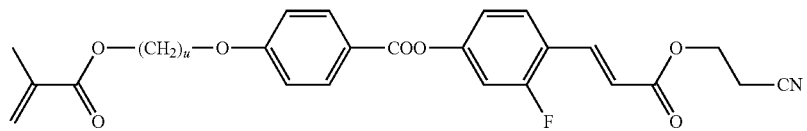
(I-20)
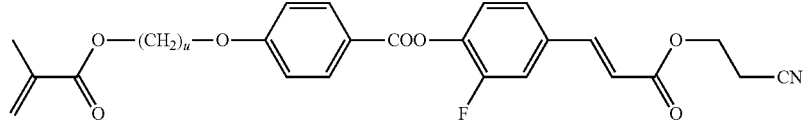
(I-21)
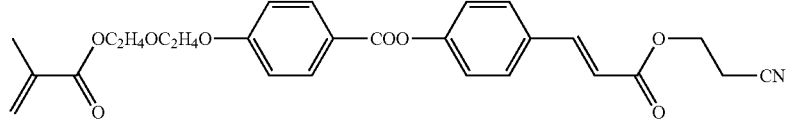
(I-22)
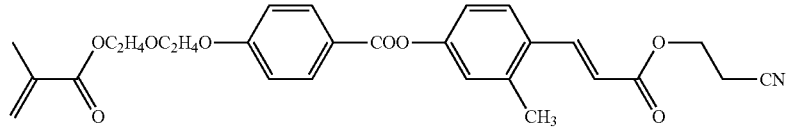
(I-23)
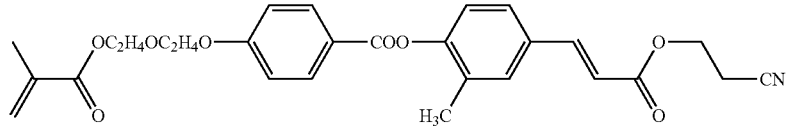
(I-24)
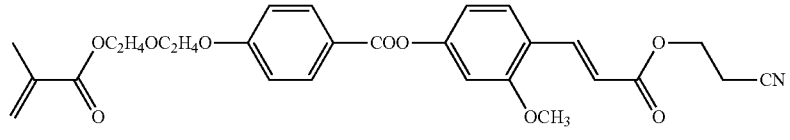
(I-25)
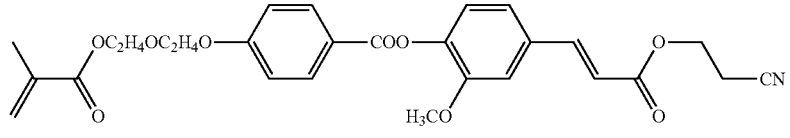
(I-26)
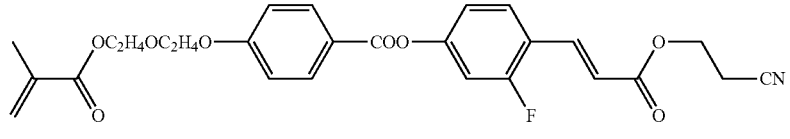
(I-27)

(I-28)
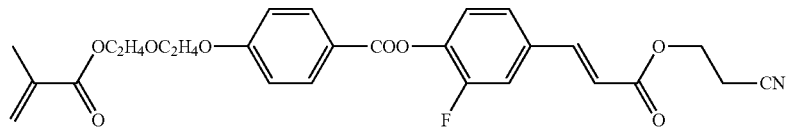
[Chem. 19]
(I-29)
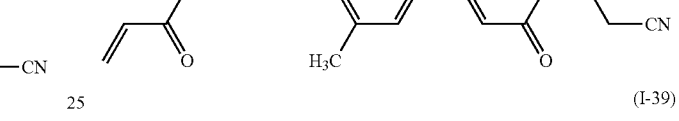
(I-30)
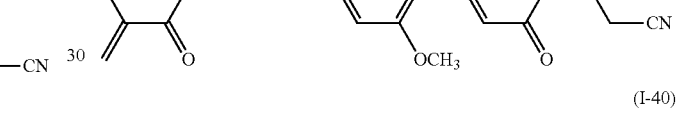
(I-31)
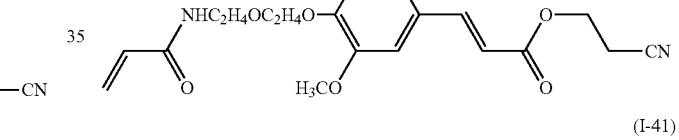
(I-32)
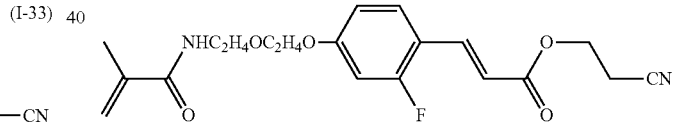
(I-33)
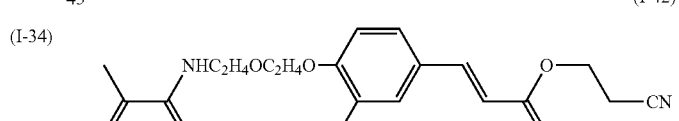
(I-34)
(I-35)
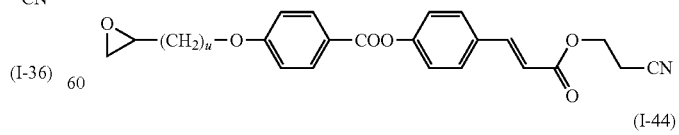
(I-36)
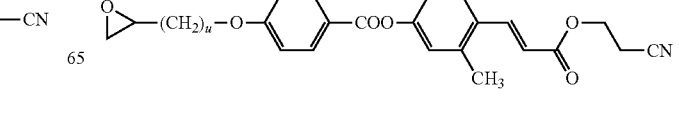
-continued
(I-37)
(I-38)
(I-39)
(I-40)
(I-41)
(I-42)
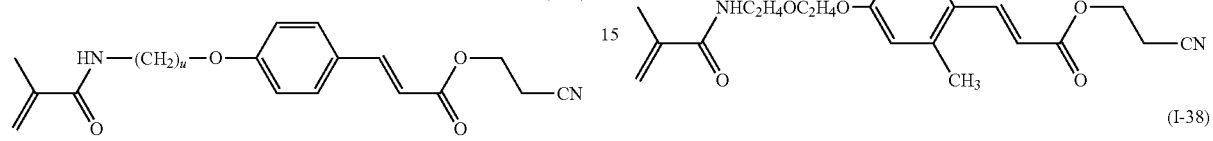
[Chem. 20]
(I-43)
(I-44)

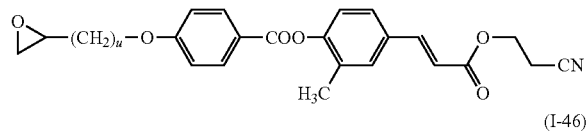
(I-45)

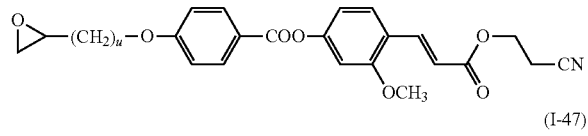
(I-46)

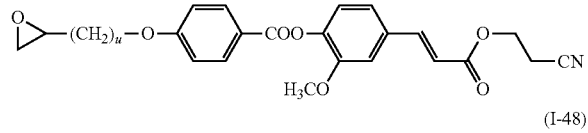
(I-47)

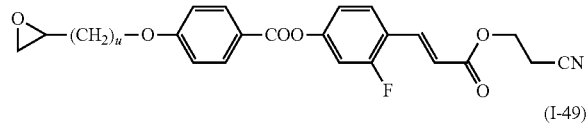
(I-48)

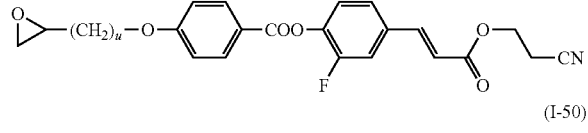
(I-49)

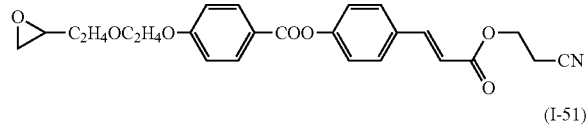
(I-50)

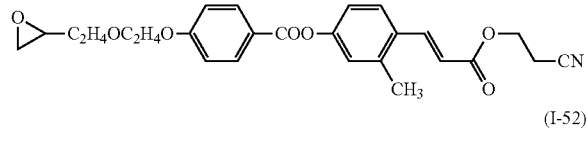
(I-51)

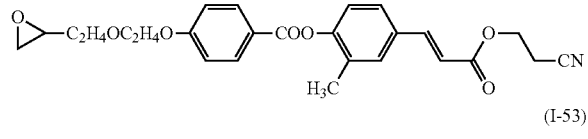
(I-52)

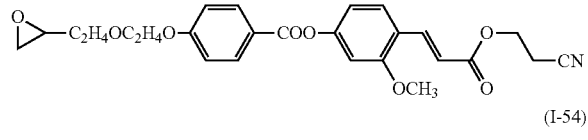
(I-53)

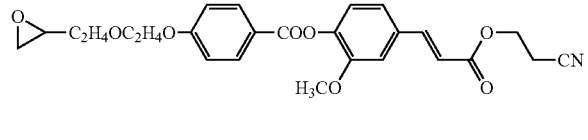
(I-54)

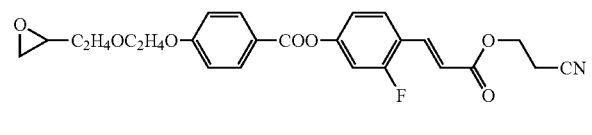
(I-56)

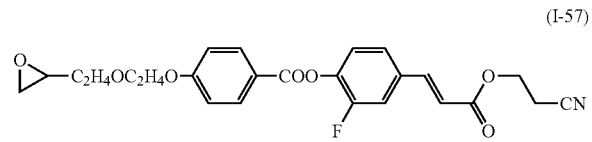
(I-57)

A polymer according to this embodiment has structural units represented by general formula (PI) below.

[Chem. 21]

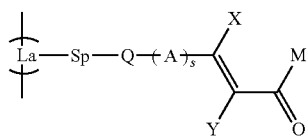
(PI)

In general formula (PI) above, La is a group derived from L in general formula (I), and Sp, Q, A, X, Y, M, and s are as defined in general formula (I) above.

The structural units represented by general formula (PI) above are preferably those represented by general formula (PIa) below, more preferably those represented by general formula (PIb) below.

[Chem. 22]

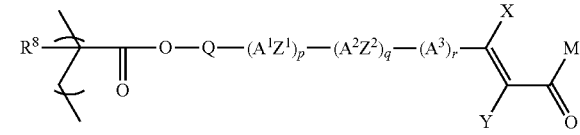
(PIa)

In general formula (PIa) above, $R^8$, Q, X, Y, M, $A^1$, $A^2$, $A^3$, $Z^1$, $Z^2$, p, q, and r are as defined in general formula (Ia). More preferably, p+q+r=2, and even more preferably, r=1 and p=1 or q=1.

[Chem. 23]

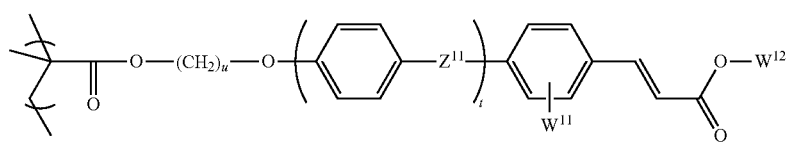
(PIb)

In general formula (PIb) above, u is an integer of 2 to 12; t is an integer of 0 or 1; $Z^{11}$ is a single bond, —COO—, or —OCO—; $W^{11}$ is hydrogen, fluorine, methyl, methoxy, ethyl, or ethoxy; and $W^{12}$ is any of general formulas ($W^{12}$-1) to ($W^{12}$-4) below.

[Chem. 24]

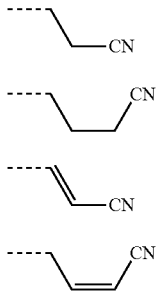

In general formula (PIb) above, $Z^{11}$ is preferably —COO—. Also preferably, u is 8 to 12, t is 1, and $W^{11}$ is methyl or methoxy, which provides good alignment with less polarized ultraviolet light for exposure. $W^{12}$ is preferably a group represented by general formula ($W^{12}$-1).

The polymer is obtained by the polymerization of a compound represented by general formula (I), (Ia), or (Ib) above or a polymerizable composition containing that compound. The polymerizable composition contains at least a compound represented by general formula (I) above and a polymerization initiator.

The polymerizable composition may contain one or a mixture of compounds represented by general formula (I), (Ia), and (Ib) above. The polymerizable composition may further contain a compound copolymerizable with compounds represented by general formula (I), (Ia), and (Ib) above.

Examples of copolymerizable compounds include those represented by general formula (VI) below, including acrylates, methacrylates, acrylamide, methacrylamide, maleates, fumarates, styrene, and derivatives thereof. Although copolymerizable compounds may be either non-liquid-crystal compounds or liquid-crystal compounds, liquid-crystal compounds are preferred.

[Chem. 25]

In general formula (VI) above, Va is a monovalent organic group, and L, Sp, and Q are as defined in general formula (I) above. If a compound, represented by general formula (VI) is used, each L, Sp, and Q in general formulas (I) and (VI) may be the same or different.

In general formula (VI) above, Va is preferably an organic group represented by general formula (VIa) below.
[Chem. 26]

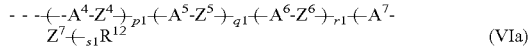

In general formula (VIa) above,
the dashed line is a linkage to Sp;
$A^4$, $A^5$, $A^6$, and $A^7$ are each independently any of trans-1,4-cyclohexylene, trans-1,3-dioxane-2,5-diyl, 1,4-naphthylene, 2,6-naphthylene, pyridine-2,5-diyl, pyrimidine-2,5-diyl, 1,2,4,5-tetrazine-2,5-diyl, 2,5-thiophenylene, 2,5-furanylene, and 1,4-phenylene, where the groups are unsubstituted, or one or more hydrogen atoms present therein are optionally replaced with fluorine, chlorine, methyl, or methoxy;

$Z^4$, $Z^5$, $Z^6$, and $Z^7$ are each independently a single bond, an alkylene group of 1 to 20 carbon atoms, —OCH$_2$—, —CH$_2$O—, —COO—, —OCO—, —CH=CH—, —CF=CF—, —CF$_2$O—, —OCF$_2$—, —CF$_2$CF$_2$—, or —C≡C—, where if one or more non-adjacent methylene groups are present in these substituents, the one or more non-adjacent methylene groups are each independently optionally replaced with —O—, —CO—, —CO—O—, —O—CO—, —Si(CH$_3$)$_2$—O—Si(CH$_3$)$_2$—, —NR$^{16}$—, —NR$^{16}$—CO—, —CO—NR$^{16}$—, —NR$^{16}$—CO—O—, —O—CO—NR$^{16}$—, —NR$^{16}$—CO—NR$^{16}$—, —CH=CH—, —C≡C—, or —O—CO—O—, where $R^{16}$ is each independently hydrogen or an alkylene group of 1 to 5 carbon atoms;

p1, q1, r1, and s1 are each independently 0 or 1; and
$R^{12}$ is hydrogen, fluorine, chlorine, cyano, or an alkyl group of 1 to 20 carbon atoms, where one or more hydrogen atoms present in the alkyl group are optionally replaced with fluorine, and if one or more non-adjacent methylene groups are present in the alkyl group, the one or more non-adjacent methylene groups are each independently optionally replaced with —O—, —CO—O—, —O—CO—, and/or —CH=CH—.

$A^4$, $A^5$, $A^6$, and $A^7$ are preferably each independently any of trans-1,4-cyclohexylene, 2,6-naphthylene, pyridine-2, 5diyl, pyrimidine-2,5-diyl, and 1,4-phenylene. Preferably, these groups are unsubstituted, or one or more hydrogen atoms present therein are replaced with fluorine, chlorine, methyl, or methoxy.

Preferably, p1+q1+r1+s1 is 0 to 3.
$R^{12}$ is preferably hydrogen, fluorine, chlorine, cyano, or an alkyl group of 1 to 18 carbon atoms. If one or more non-adjacent methylene groups are present in the alkyl group, the one or more non-adjacent methylene groups are optionally replaced with —O—, —CO—O—, —O—CO—, and/or —CH=CH—.

The copolymerizable compound, if used, is preferably present in an amount of 0.1 to 30 mol, more preferably 0.2 to 10 mol, even more preferably 0.3 to 5 mol, per 100 mol of the compound represented by general formula (I) above.

The structural units may be arranged in the copolymer in any sequence and with any randomness.

The polymerization initiator may be any known polymerization initiator selected depending on the type of polymerization of the polymerizable group. Examples of polymerization initiators include those listed in the following known literature: "Synthesis and Reactions of Polymers" (The Society of Polymer Science, Japan, Kyoritsu Shuppan Co., Ltd.).

Examples of thermal polymerization initiators for radical polymerization include azo compounds such as azobisisobutyronitrile and peroxides such as benzoyl peroxide.

Examples of photopolymerization initiators include aromatic ketones such as benzophenone, Michler's ketone, xanthone, and thioxanthone; quinones such as 2-ethylanthraquinone; acetophenones such as acetophenone, trichloroacetophenone, 2-hydroxy-2-methylpropiophenone, 1-hydroxycyclohexyl phenyl ketone, benzoin ether, 2,2-diethoxyacetophenone, and 2,2-dimethoxy-2-phenylacetophenone; diketones such as benzil and methyl benzoylformate; acyloxime esters such as 1-phenyl-1,2-propandione-2-(O-benzoyl)oxime; acylphosphine oxides such as 2,4,6-trimethylbenzoyldiphenylphosphine oxide; sulfur compounds such as tetramethylthiuram and dithiocarbamate; organic peroxides such as benzoyl peroxide; and azo compounds such as azobisisobutyronitrile.

Examples of thermal polymerization initiators for cationic polymerization include aromatic sulfonium salts.

Examples of photopolymerization initiators include organic sulfonium salts, iodonium salts, and phosphonium compounds.

The polymerization initiator is preferably present in the polymerizable composition in an amount of 0.1% to 10% by mass, more preferably 0.1% to 6% by mass, even more preferably 0.1% to 3% by mass.

The polymerizable composition may be polymerized in the presence of a solvent. Examples of solvents include benzene, toluene, xylene, ethylbenzene, pentane, hexane, heptane, octane, cyclohexane, cycloheptane, methanol, ethanol, 1-propanol, 2-propanol, ethylene glycol, ethylene glycol monomethyl ether, ethylene glycol dimethyl ether, 2-butanone, acetone, tetrahydrofuran, γ-butyrolactone, N-methyl-pyrrolidone, dimethyl sulfoxide, and dimethylformanide. These organic solvents may be used alone or in combination.

After a polymerization reaction is performed in a reaction vessel such as a glass or stainless steel vessel, the product can be purified to obtain a polymer.

The polymer preferably has a weight average molecular weight of 80,000 to 500,000, more preferably 150,000 to 450,000, even more preferably 250,000 to 400,000. The weight average molecular weight is measured by gel permeation chromatography and is expressed relative to polystyrene standards. The measurement conditions are as specified in the Examples disclosed herein.

The polymer preferably has a molecular weight distribution Mw/Mn of 1.2 to 6.0, more preferably 1.4 to 4.0. As used herein, the symbols "Mw" and "Mn" refer to the weight average molecular weight and number average molecular weight, respectively, measured by gel permeation chromatography, Preferably $Z^4$, $Z^5$, and $Z^6$, and $Z^7$ are each independently —NR—CO—, —CO—NR—, —NR—CO—O—, —O—CO—NR—, —NR—CO—NR—, or —O—CO—O—, and $A^4$, $A^5$, $A^6$, and $A^7$ are each independently 1,4-naphthylene, 2,6-naphthylene, pyridine-2,5-diyl, pyrimidine-2,5-diyl, 2,5-thiophenylene, 2,5-furanylene, or 1,4-phenylene. This improves the thermal stability of alignment on the liquid crystal alignment layer according to this embodiment.

Also preferably, $Z^4$, $Z^5$, $Z^6$, and $Z^7$ are each independently —OCH$_2$—, —CH$_2$O—, —CF$_2$O—, —OCF$_2$—, —CF$_2$CF$_2$—, —NR—, or —CO—, and $A^4$, $A^5$, $A^6$, and $A^7$ are each independently trans-1,4-cyclohexylene, 1,4-naphthylene, 2,6-naphthylene, of 2,5-furanylene. This improves the solubility of the polymer according to this embodiment.

Also preferably, $Z^4$, $Z^5$, $Z^6$, and $Z^7$ are each independently a singe bond, —OCH$_2$—, —CH$_2$O—, —COO—, —OCO—, or —C≡C—, $A^4$, $A^5$, $A^6$, and $A^7$ are each independently trans-1,4-cyclohexylene, trans-1,3-dioxane-2,5-diyl, or 1,4-phenylene, and $R^{12}$ is an alkyl group of 1 to 20 carbon atoms, an alkoxy group, fluorine, trifluoromethyl, or trifluoromethoxy. This allows a pretilt angle of 80° or more to be induced to the liquid crystal alignment layer according to this embodiment.

Preparation of Polymer for Liquid Crystal Alignment Layer

The compound (particularly, a cinnamic acid derivative) according to this embodiment may be used alone as a raw material for polymers or may be mixed with other monomers for use as a polymerizable composition. The composition may be prepared by mixing the cinnamic acid derivative and other monomers in any ratio.

The polymer according to this embodiment may also be prepared by dissolving the above compound or a polymerizable composition containing that compound in a solvent, applying the solution to a substrate, drying the coating to remove the solvent, and performing a polymerization reaction by heating or light exposure.

Method for Forming Liquid Crystal Alignment Layer

Since the polymer according to this embodiment has cyano groups and photoreactive structures (e.g., cinnamic acid backbones), a layer containing the polymer can be exposed to light to achieve both an anchoring force on liquid crystal molecules and the thermal stability of the anchoring force. A layer formed by light exposure can be referred to as "liquid crystal alignment layer (photoalignment layer)".

The liquid crystal alignment layer (photoalignment layer) can be formed, for example, by the following method of manufacture. A method for manufacturing the liquid crystal alignment layer includes the steps of forming a resin layer containing the polymer according to this embodiment on a substrate (resin-layer forming step) and exposing the resin layer to light (light exposure step).

The resin layer can be formed by preparing a polymer solution containing the polymer according to this embodiment and a solvent and applying the solution to a substrate. The application may be followed by the step of removing the solvent.

The removal of the solvent after the application is preferably performed by heating the coated surface. The drying temperature is preferably 50+ C. to 300° C., more preferably 80° C. to 200° C. The drying time is preferably 2 to 200 minutes, more preferably 2 to 100 minutes, The resulting resin layer may be exposed to light to induce an anchoring force (orientation control capability) to the resin layer and thereby to obtain a liquid crystal alignment layer. The liquid crystal alignment layer can be evaluated for its anchoring force, for example, by measuring the azimuthal anchoring energy at the interface between a liquid crystal phase containing liquid crystal molecules and the liquid crystal alignment layer. The azimuthal anchoring energy at the interface between the liquid crystal phase and the liquid crystal alignment layer is preferably 100 μJ/m$^2$ or more, more preferably 150 μJ/m$^2$ or more, even more preferably 250 μJ/m$^2$ or more.

Preferred solvents for use in the polymer solution are those that dissolve but do not react with the polymer according to this embodiment and other optional components described later. Examples of solvents include 1,1,2-trichloroethane, N-methylpyrrolidone, butoxyethanol, γ-butyrolactone, ethylene glycol, polyethylene glycol monomethyl ether, propylene glycol 2-pyrrolidone, N,N-dimethylformamide, dimethylformamide, phenoxyethanol, tetrahydrofuran, dimethyl sulfoxide, methyl isobutyl ketone, and cyclohexanone. These solvents may be used alone or in combination.

The polymer solution may optionally contain other components, including siloxane derivatives for improving the adhesion to substrates such as glass substrates, leveling agents for improving the leveling of coatings, ultraviolet absorbers and light stabilizers for improving light fastness, and antioxidants and polymerization inhibitors for improving the storage stability of materials.

The polymer solution for use in the method for manufacturing the liquid crystal alignment layer may be replaced with a monomer solution containing a compound represented by general formula (I) according to this embodiment (particularly, a cinnamic acid derivative) and a solvent. Specifically, the resin layer may be formed by applying the monomer solution to a substrate and polymerizing the monomer in the coating by heating or light exposure to form a polymer. In this case, the formation of the polymer and the induction of an anchoring force may be simultaneously performed.

Examples of solvents for use in the monomer solution Include those illustrated for the polymer solution.

The formation of the polymer and the induction of an anchoring force may be simultaneously performed with a combination of heat and light or with a combination of light components with two or more different wavelengths. In this case, the monomer solution preferably contains a polymerization initiator. After the application, the solvent may be removed, and the coating may be exposed to unpolarized light to form a polymer by photopolymerization.

If the polymer is formed by thermal polymerization, the heating temperature may be any temperature sufficient for the polymerization to proceed, typically about 50° C. to 250° C. more preferably about 70° C. to 200° C.

If the polymer is formed by photopolymerization, unpolarized ultraviolet light is preferably used for light exposure. The exposure energy is preferably 10 to 8,000 mJ/cm$^2$, more preferably 40 to 5,000 mJ/cm$^2$. The exposure intensity is preferably 2 to 1,000 mW/cm$^2$, more preferably 4 to 500 mW/cm$^2$. The exposure wavelength preferably peaks in the range of 250 to 450 nm.

Examples of substrates include glass, silicon, polyethylene terephthalate, polybutylene terephthalate, polyethersulfone, polycarbonate, and triacetylcellulose substrates. These substrates may have various layers formed thereon, such as electrode layers (conductive layers), color filter layers, and liquid crystal alignment layers.

Examples of electrode layers (conductive layers) include Cr, Al, ITO (e.g., $In_2O_3$—$SnO_2$), and NESA ($SnO_2$) layers. These electrode layers may be patterned by photoetching. The electrode layers may also be patterned by other techniques such as the use of a mask in the formation of the electrode layers.

If a substrate having a liquid crystal alignment layer formed thereon in advance is used in the method for manufacturing the liquid crystal alignment layer, a photoalignment layer according to this embodiment may be further formed on the substrate to newly induce the capability of controlling the direction and angle of orientation to the substrate.

The application may be performed, for example, by processes such as spin coating, die coating, gravure coating, flexography, and inkjet printing.

The solid content of the polymer solution is preferably 0.51 to 10% by mass, and may be selected depending on, for example, the method for applying the solution to the substrate, viscosity, and volatility.

In the step of exposing the resin layer to light, the resin layer containing the polymer according to this embodiment is exposed to linearly polarized light in the direction normal to the surface of the resin layer and/or to unpolarized or linearly polarized light in an oblique direction. This light exposure causes a photocrosslinking reaction (e.g., a dimerization reaction of a cinnamic acid derivative) and thereby cures the resin layer to induce an anchoring force.

To induce the desired pretilt angle, it is preferred to expose the surface of the resin layer to linearly polarized light, in an oblique direction. The term "oblique direction" refers to a tilt from the direction parallel to the substrate surface, and the angle of this tilt is referred to as "pretilt angle". The pretilt angle can be adjusted depending on the application. For vertical alignment layers, the pretilt angle is generally preferably 70° to 89.8°. For horizontal alignment layers, the pretilt angle is generally preferably 1° to 7°. In particular, the pretilt angle is preferably 0° to 1° for IPS mode.

Examples of light sources that can be used include xenon lamps, high-pressure mercury lamps, super-high-pressure mercury lamps, and metal halide lamps. Light emitted from these light sources can be passed through polarizing filters or prisms to obtain linearly polarized light. Ultraviolet or visible light emitted from these light sources can be passed through filters such as interference filters and color filters to achieve a limited wavelength range for exposure.

The exposure energy is preferably 15 to 500 mJ/cm$^2$, more preferably 20 to 300 mJ/cm$^2$. The exposure intensity is preferably 2 to 500 mW/cm$^2$, more preferably 5 to 300 mW/cm$^2$.

To cure the resin layer by a photocrosslinking reaction, it may be exposed to, for example, ultraviolet or visible light containing light with a wavelength of 150 to 800 nm. Ultraviolet light with a wavelength of 270 to 4 50 nm is preferred. If the compound according to this embodiment (particularly, a cinnamic acid derivative) contains a naphthylene group, an anchoring force can be more efficiently induced by exposure to ultraviolet light, with a wavelength of 270 to 450 nm. This effect is attributed to the fact that naphthylene groups well absorb ultraviolet light with a wavelength of 270 to 450 nm.

The liquid crystal alignment layer (photoalignment layer) preferably has a thickness: of about 10 to 250 nm, more preferably about 10 to 100 nm.

Method for Manufacturing Liquid Crystal Display Device

The liquid crystal alignment layer according to this embodiment can be used, for example, in liquid crystal cells and liquid crystal display devices. A liquid crystal alignment layer (photoalignment layer) manufactured by the method described above can be used to manufacture a liquid crystal cell including a liquid crystal composition held between a pair of substrates and a liquid crystal display device including such a liquid crystal cell, for example, as follows.

A liquid crystal cell manufactured with the liquid crystal alignment layer according to this embodiment includes a liquid crystal disposed between two substrates. The liquid crystal alignment layer according to this embodiment is formed on at least one of the substrates.

An example method for manufacturing a liquid crystal cell will now be described. This method uses two substrates each of which has the liquid crystal alignment layer according to this embodiment.

Two substrates are first placed such that the liquid crystal alignment layers thereof face each other. The peripheries of the two substrates are then bonded together with a sealant such that a predetermined gap (cell gap) is maintained therebetween. A liquid crystal is then injected into the cell gap defined by the liquid crystal alignment layers and the sealant, for example, by vacuum filling. The injection hole is sealed off to obtain a liquid crystal cell.

The liquid crystal cell can also be manufactured by a technique called one-drop filling (ODF). A sealant such as an ultraviolet-curable sealant is first applied to a predetermined area on the liquid crystal alignment layer formed on one substrate, and a liquid crystal is dispensed dropwise to the area surrounded by the sealant on the liquid crystal alignment layer. The other substrate is then bonded such that the liquid crystal alignment layers thereof face each other. The sealant is then cured by exposing the entire substrates to ultraviolet light to obtain a liquid crystal cell.

No matter which of the two methods is used to manufacture a liquid crystal cell, it is desirable to remove flow orientation during injection by heating the liquid crystal to the temperature at which the liquid crystal transitions to an isotropic phase and then allowing it to cool to room temperature. During the cooling process, the liquid crystal is realigned by the anchoring force of the liquid crystal alignment layers.

The sealant may be, for example, epoxy resin,

To maintain a uniform cell gap, beads such as silica gel, alumina, or acrylic beads may be disposed between the two substrates before they are bonded to each other. These beads may be dispersed over the liquid crystal alignment layers or may be mixed in the sealant.

The liquid crystal used to fill the liquid crystal cell may be, for example, a nomadic liquid crystal.

Liquid crystals with negative dielectric anisotropy are preferred for vertically aligned liquid crystal cells. Examples of such liquid crystals include dicyanobenzene, pyridazine, Schiff base, azoxy, naphthalene, biphenyl, and phenylcyclohexane liquid crystals. These liquid crystals may be used alone or in combination. Typically, two or more liquid crystals are used in combination depending on the desired performance.

Liquid crystals with positive dielectric anisotropy are preferred for horizontally aligned liquid crystal cells. Examples of such liquid crystals include cyanobenzene, difluorobenzene, trifluorobenzene, trifluoromethylbenzene, trifluoromethoxybenzene, pyrimidine, naphthalene, biphenyl, and phenylcyclohexane liquid crystals. These liquid crystals may be used alone or in combination. Typically, two or more liquid crystals are used in combination depending on the desired performance.

Polarizers are bonded to the cater surfaces of the thus-manufactured liquid crystal cell to obtain a liquid crystal display device.

Examples of polarizers include H-sheet polarizers, which are produced by incorporating iodine into polyvinyl alcohol during stretch orientation, and those sandwiched between cellulose acetate protective layers.

A liquid crystal display device including the liquid crystal alignment layer according to this embodiment has superior properties such as good display characteristics and high reliability because of the large anchoring force of the liquid crystal alignment layer. The liquid crystal alignment layer can be used to manufacture both a horizontally aligned liquid crystal device and a vertically aligned liquid crystal device.

Method for Manufacturing Optically Anisotropic Material

An optically anisotropic material can be manufactured by applying a polymerizable liquid crystal composition to the liquid crystal alignment layer (photoalignment layer) according to this embodiment and polymerizing polymerizable liquid crystal, molecules (liquid crystal molecules that can be polymerized) in the polymerizable liquid crystal composition in an aligned state. The term "optically anisotropic material" refers to a material that varies m optical properties such as light propagation speed, refractive index, and absorption depending on the direction in which light travels through the material.

The polymerizable liquid crystal composition is a composition containing a polymerizable liquid crystal. The polymerizable liquid crystal composition may be either a single polymerizable liquid crystal compound or a mixture with other liquid crystal compounds and shows liquid crystallinity. Examples of polymerizable liquid crystal compositions include calamitic polymerizable liquid crystal compounds containing a rigid segment, known as a mesogen that is composed of a series of structures such as 1,4-phenylene and 1,4-cyclohexylene, and a polymerizable functional group such as (meth)acryloyloxy, vinyloxy, and epoxy, including those disclosed in "Handbook of Liquid Crystals" (D. Demos, J. W. Goodby, G. W. Gray, H. W. Spiess, and V. Vill, Wiley-VCH, 1998), "Chemistry of Liquid Crystal" (Kikan Kagaku Sosestu No. 22) (The Chemical Society of Japan, 1994), and Japanese Unexamined Patent Application Publication Nos. 7-294735, 8-3111, 8-29618, 11-80090, 11-148079, 2000-178233, 2002-308831, and 2002-145830; calamitic polymerizable liquid crystal compounds containing a maleimide group, including those disclosed in Japanese Unexamined Patent Application Publication Nos. 2004-2373 and 2004-99446; calamitic polymerizable liquid crystal compounds containing an allyl ether group, including those disclosed in Japanese Unexamined Patent Application Publication Mo. 2004-149522; and discotic polymerizable compounds, including those disclosed in "Handbook of Liquid Crystals" (D. Demus, J. W. Goodby, G. W. Gray, H. W. Spiess, and V. Vill, Wiley-VCH, 1998), "Chemistry of Liquid Crystal" (Kikan Kagaku Sosestu No. 22) (The Chemical Society of Japan, 1994), and Japanese Unexamined Patent Application Publication No. 07-146409. Calamitic liquid crystal compounds containing a polymerizable group are preferred since a liquid crystal temperature range including low temperatures around room temperature can readily be achieved.

EXAMPLES

The present invention is further illustrated by the following examples, although these examples are not intended to limit the invention. The structures of compounds were determined by techniques such as mass spectroscopy (MS) and nuclear magnetic resonance (NMR) spectroscopy. Parts and percentages are by mass unless otherwise specified.

Synthesis of Monomer

Example 1

Synthesis of Monomer I-1-1

A target compound (Monomer I-1-1) was synthesized by a procedure represented by the following formula via Intermediate Compounds 1 to 6.

[Chem. 27]

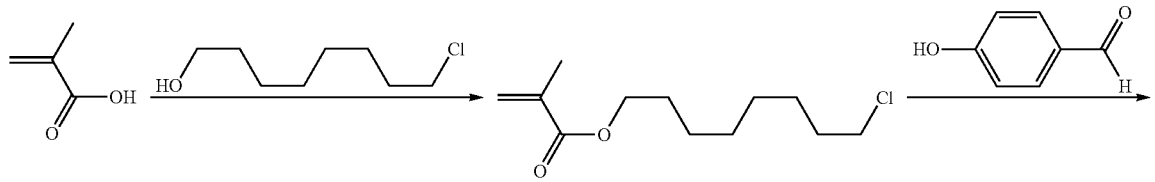

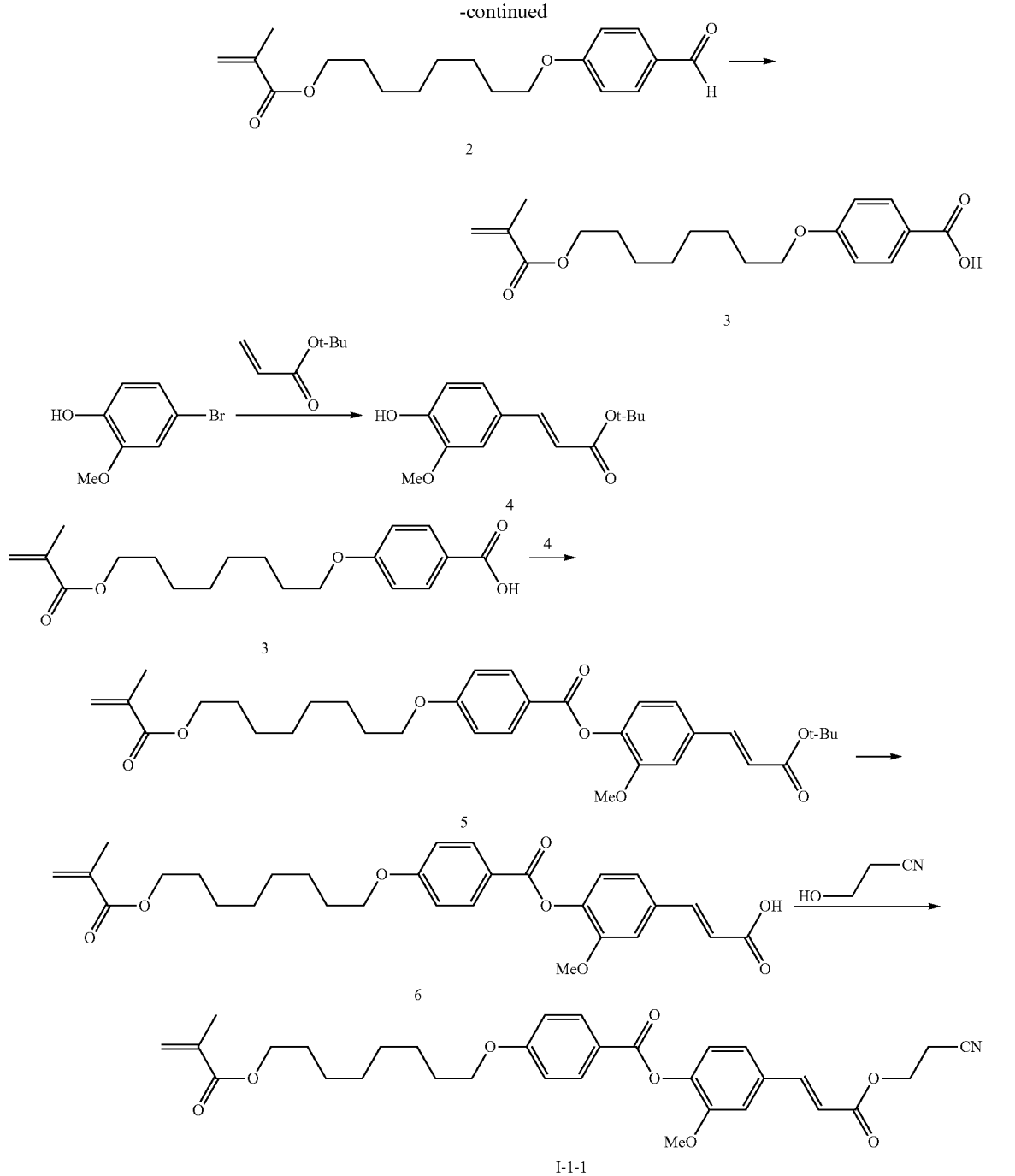
Synthesis of Compound 1
[Chem. 28]
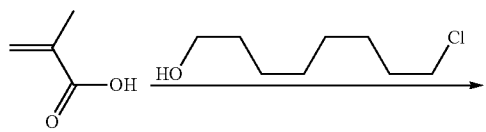
In 450 mL of cyclohexane were dissolved 193 g (1.21 mol) of 8-chlorooctanol, 158.3 g (1.84 mol) of methyl methacrylate, 1.5 g of 4-methoxyphenol, and 22.8 g (0.12 mol) of p-toluenesulfonic acid, and the solution was heated under reflux for 6 hours. The reaction solution was allowed to cool to room temperature. The solution was washed with water three times, was washed with saturated aqueous sodium hydrogen carbonate solution three times, and was washed with brine twice. The solution was dried over anhydrous sodium sulfate, and the solvent was distilled off to obtain 258 g of Compound 1 (8-chlorooctyl methacrylate) as a colorless transparent liquid. The purify was 99% (GC).

EI-MS: 232 (M$^+$)

Synthesis of Compound 2

[Chem. 29]

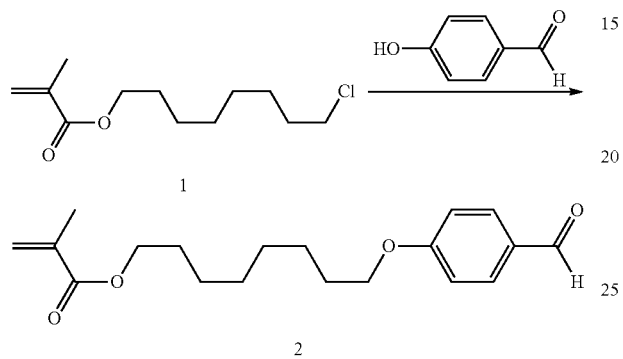

In 500 ml of dimethylformamide were dissolved 34.6 g (0.284 mol) of 4-hydroxybenzaldehyde, 49 g (0.341 mol) of potassium carbonate, and 0.1 g of 18-crown-6. To the solution, 58 g (0.284 mol) of 8-chlorooctyl methacrylate was added at room temperature in a nitrogen atmosphere. The reaction solution was heated to 90° C. and was stirred for 6 hours. After the reaction was determined to be complete by GC, the reaction solution was allowed to cool to room temperature and was filtered. To the solution were added 200 mL of ethyl acetate and 200 ml of water, and the solution was filtered again. The organic and aqueous layers were separated, and the aqueous layer was extracted with ethyl acetate three times. All the organic layers were combined and washed with brine three times. The organic layer was dried over anhydrous sodium sulfate, and the solvent was distilled off to obtain Compound 2 as a crude product. The resulting product, i.e., Compound 2, was used for the next reaction without purification.

EI-MS: 318 (M$^+$)

Synthesis of Compound 3

[Chem. 30]

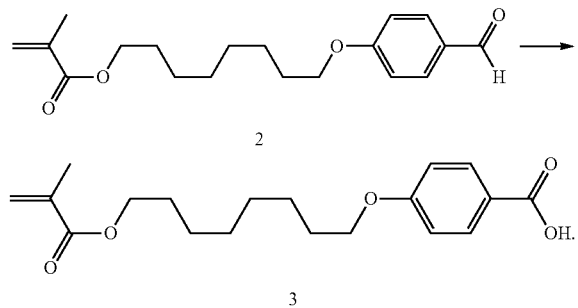

In 60 mL of water and 350 mL of acetonitrile were dissolved 50 g (about 0.14 mol) of Compound 2, 4.43 g (0.029 mol) of sodium dihydrogen phosphate, and 16 g of 30% aqueous hydrogen peroxide, and the solution was cooled in ice. To the reaction solution, was added dropwise a dilution of 23 g of 78% sodium chlorite with 200 mL of water, and the reaction solution was stirred at room temperature overnight. The reaction was determined to be complete by HPLC. To the reaction solution, 10% hydrochloric acid was added until a pH of 1 was: reached. The resulting white precipitate was filtered off and was washed with water three times. The resulting solid was dissolved in dichloromethane, and the solution was dried over anhydrous sodium sulfate, heptane was added to the solution, and dichloromethane was distilled off under reduced pressure. The resulting precipitate was filtered off to obtain 30 g of the target compound, i.e., Compound 3. The purity was 99% (HPLC), Synthesis of Compound 4

[Chem. 31]

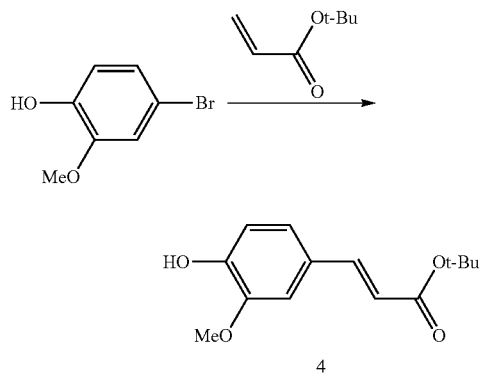

In 700 mL of N-methylpyrrolidone were dissolved 50 g (0.24 6 mol) of 4-bromo-2-methoxyphenol, 47.2 g (0.369 mol) of t-butyl acrylate, and 50.9 g (0.369 mol) of potassium carbonate, and the system was purged with nitrogen. To the reaction solution was added 0.055 g (0.246 mmol) of palladium acetate, and the system was purged with nitrogen again and was stirred at 130°0 C. for 6 hours. The reaction was determined to be complete by HPLC. The reaction solution was allowed to cool, to room temperature, and 300 mL of ethyl acetate and 300 mL of 5% hydrochloric acid were added to the solution. The organic and aqueous layers were separated, and the aqueous layer was extracted with ethyl acetate three times. All the combined organic layers were combined and washed with brine three times, and the organic layer was dried over anhydrous sodium sulfate. The solvent was distilled off, and 80 g of silica gel was added to obtain a slurry. The slurry was fed into a column filled with 100 g of alumina and 300 g of silica gel and was eluted with a mixture of ethyl acetate and heptane. The solvent was distilled off, and the resulting crude crystal was recrystallized from heptane to obtain 43.2 g of Compound 4 as a white solid. The purity was 99% (HPLC).

EI-MS: 250 (M$^+$)

Synthesis of Compound 5

[Chem. 32]

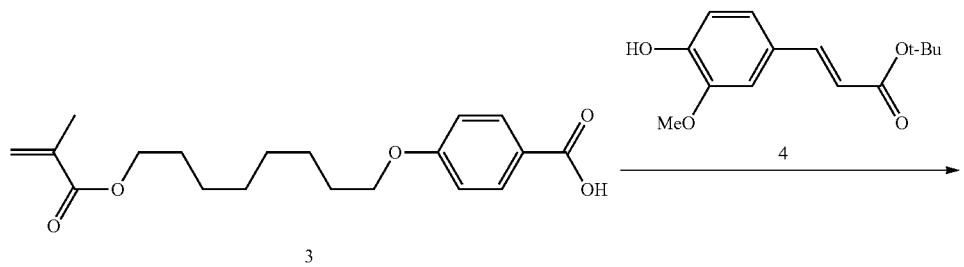

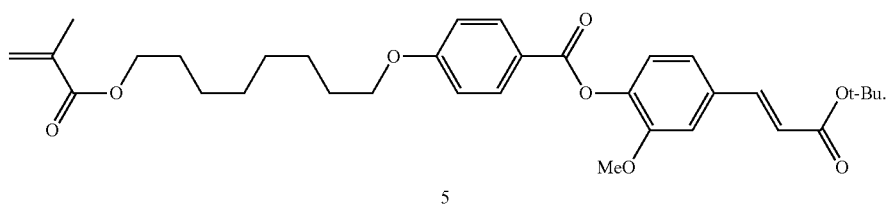

In 400 mL of dichloromethane were dissolved 22.3 g (0.06676 mol) of Compound 3, 16.7 g (0.06677 mol) of Compound 4, and 1.22 g (10 mmol) of 4-dimethylaminopyridine, and the system was purged with nitrogen and was cooled in ice. To the reaction solution was added dropwise a solution of 12.6 g (0.1 mol) of N,N'-diisopropylcarbodiimide in 100 mL of dichloromethane, and the solution was stirred at room temperature overnight. The reaction solution was filtered. The reaction solution was washed with 200 mL of 10% hydrochloric acid, was washed with 200 mL of brine three times, and was dried over anhydrous magnesium sulfate. The solvent was distilled off to some extent, and 70 g of silica gel was added to obtain a slurry. The slurry was fed into a column filled with 100 g of alumina and 200 g of silica gel and was eluted with dichloromethane. The solvent was distilled off, and the resulting solid was recrystallized from a mixture of ethyl acetate and heptane to obtain 31.8 g of the target compound, i.e., Compound 5, as a white solid. The purity was 99% (HPLC).

EI-MS: 566 (M$^+$)

Synthesis of Compound 6

[Chem. 33]

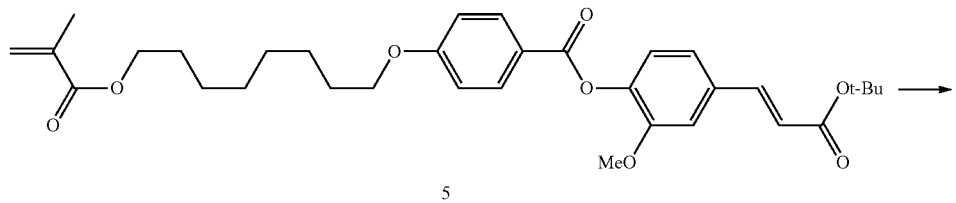

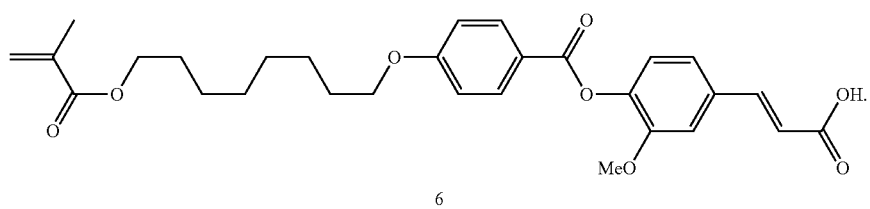

In 200 mL of dichloromethane was dissolved 31.8 g (0.0562 mol) of Compound 5, and the system was purged with nitrogen and was cooled in ice. To the system was added dropwise 32 g (0.280 mol) of trifluoroacetic acid, and the solution was stirred at room temperature overnight. The reaction was determined to be complete by HPLC. To the reaction solution was added 300 mL of heptane, and the solvent was distilled off to precipitate a solid, followed by filtration. The resulting solid was washed with water and heptane to obtain 26 g of the target compound, i.e., Compound 6, as a colorless crystal. The purity was 99% (HPLC).

Synthesis of Compound I-1-1

[Chem. 34]

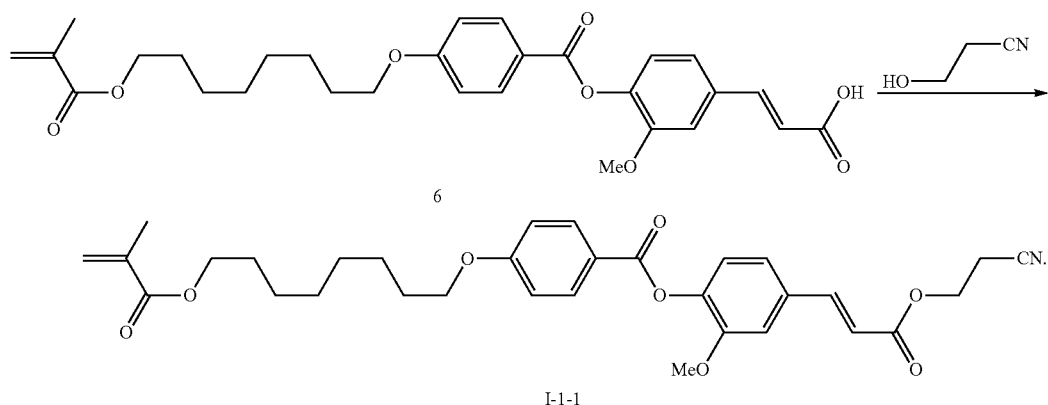

In 200 mL of dichloromethane was dissolved 22.9 g (45 mmol) of Compound 6, 4.9 g (0.04 mol) of 3-hydroxypropionitrile, and 0.70 g (5.6 mmol) of 4-dimethylaminopyridine, and the system was purged with nitrogen and was cooled in ice. To the reaction solution was added dropwise a solution of 7.87 g (64 mmol) of N,N'-diisopropylcarbodiimide in 50 mL of dichloromethane, and the solution was stirred at room temperature overnight. The reaction solution was filtered. The reaction solution was washed with 100 mL of 10% hydrochloric acid, was washed with 100 mL of brine three times, and was dried over anhydrous magnesium sulfate. The solution was purified with a column filled with 30 g of alumina and 300 g of silica gel and a mixture of ethyl acetate and dichloromethane. The solvent was distilled off, and the resulting solid was recrystallized from methanol to obtain 16.4 g of the target compound, i.e., Monomer I-1-1, as a white solid. The purity was 99.5% (HPLC).

EI-MS: 563 (M$^+$)

Comparative Example 1

Synthesis of Compound R-1

[Chem. 35]

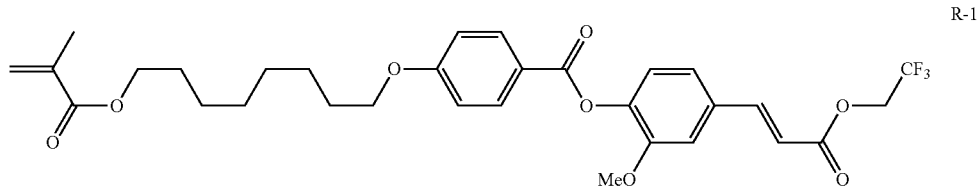

Compound R-1 was synthesized by the same procedure as Compound I-1-1 in Example 1 except that 4.9 g (0.04 mol) of 3-hydroxypropionitrile was replaced with 2,2,2-trifluoroethanol.

EI-MS: 592 (M+)

Comparative Example 2

Synthesis of Compound R-2

[Chem. 36]

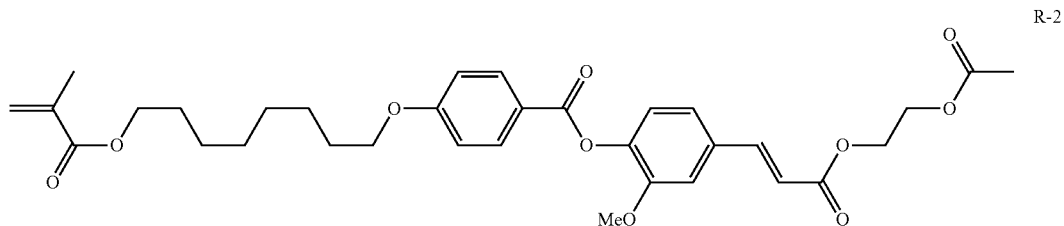

R-2

Compound R-2 was synthesized by the same procedure as Compound I-1-1 in Example 1 except that 4.9 g (0.04 mol) of 3-hydroxypropionitrile was replaced with 2-hydroxyethylacetic acid.

EI-MS; 596 (M+)

Comparative Example 3

Synthesis of Compound R-3

[Chem. 37]

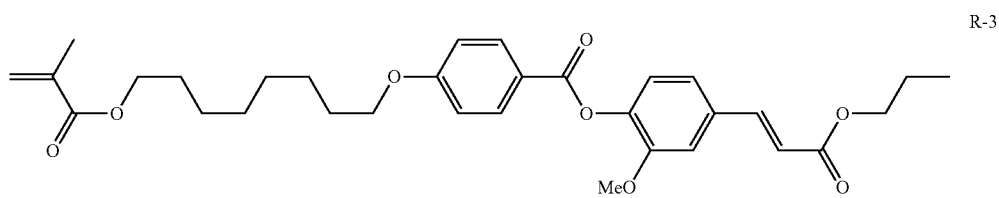

R-3

Compound R-3 was synthesized by the same procedure as Compound I-1-1 in Example 1 except that 4.9 g (0.04 mol) of 3-hydroxypropionitrile was replaced with 1-propanol.

EI-MS: 552 (M+)

Example 2

Synthesis of Monomer I-1-2

A target compound (Monomer I-1-2) was synthesized by a procedure represented by the following formula via Intermediate Compounds 11 to 16. The same procedure as in Example 1 was performed except that methyl methacrylate, serving as a starting material, was replaced with acrylate to obtain the target compound, i.e., Monomer I-1-2, as a white solid. The purity was 99.5% (HPLC).

EI-MS; 549 (M+)

[Chem. 38]

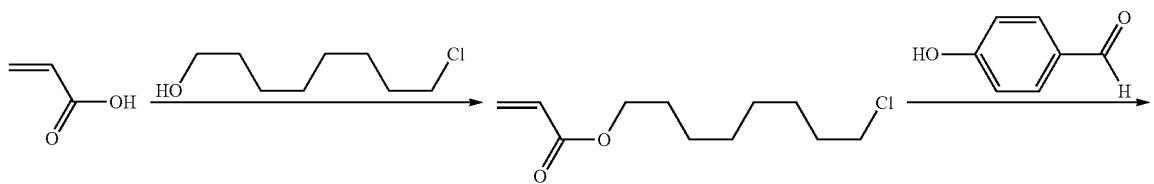

11

-continued
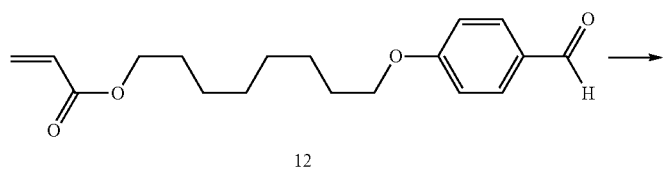
12
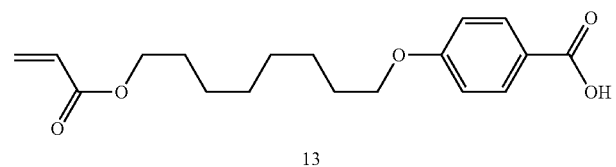
13
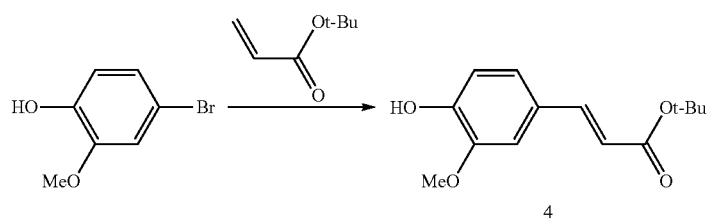
4
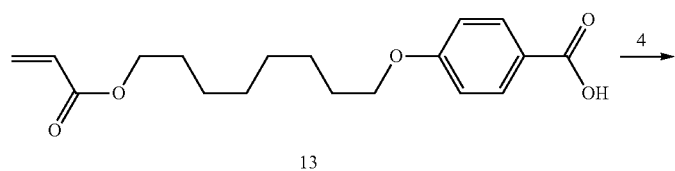
13
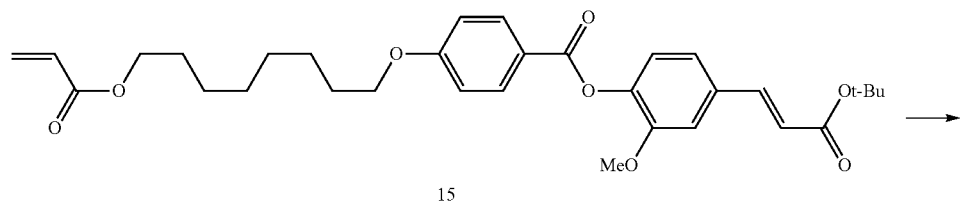
15
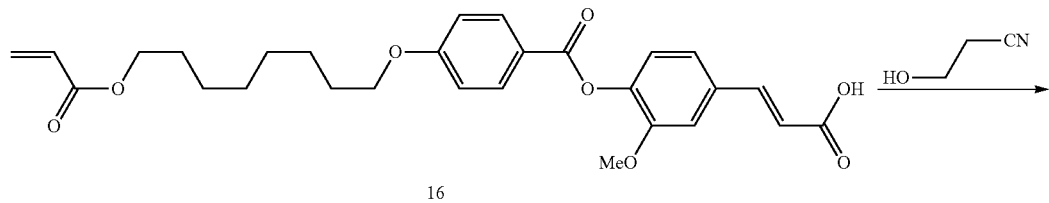
16
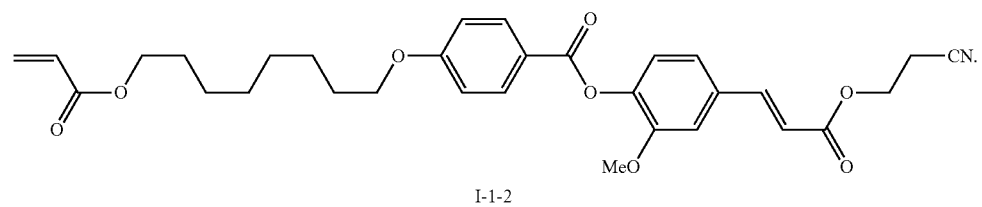
I-1-2

Polymerization of Cinnamic Acid Derivative Monomer

Example 2

Synthesis of Polymer P-I-1-1

[Chem. 39]

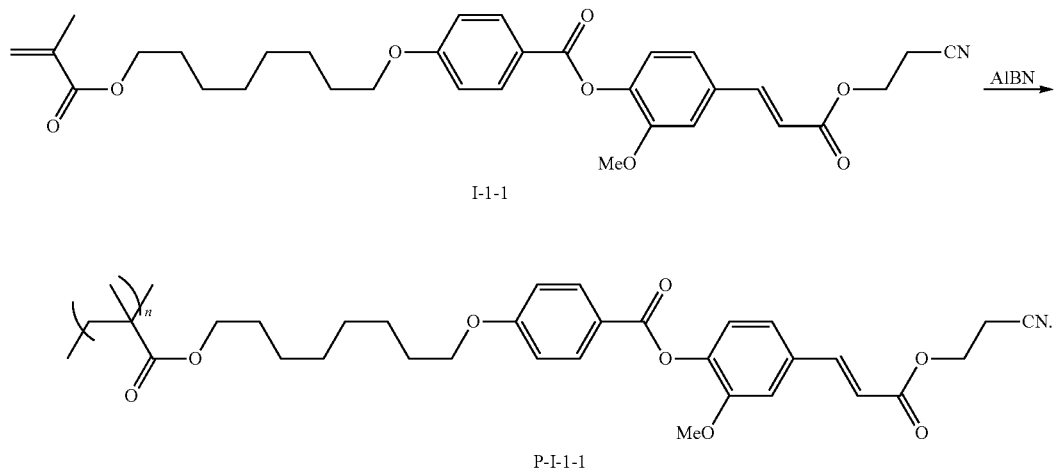

In 82.5 mL of THF were dissolved 16.5 g of Monomer I-1-1 and 92 mg of AIBN, and the solution was reacted in a nitrogen atmosphere at 55°C. for 6 hours. The target compound was precipitated from the resulting solution with hexane. The precipitate was dried under reduced pressure to obtain 11 g of the target compound, i.e., Polymer P-I-1-1. This polymer had a weight average molecular weight of 198,000.

Weight Average Molecular Weight Measurement

The weight average molecular weight was measured by gel permeation chromatography (GPC) under the following measurement conditions.

The measurement system was a Tosoh HLC-8220 GPC system equipped with four series-connected analysis columns, i.e., two TSKgel GMHXL columns, one TSKgel G2000XL column, and one TSKgel G1000XL, and a differential refractive index (RI) detector. A calibration curve was obtained from Shows Denko STANDARD SM-105 polystyrene standards (molecular weight range: 1,300 to 3,800,000). The resulting polymer was dissolved in THF to a concentration of 1 μg/mL. The mobile phase was THF. The feed rate was 1 mL/min. The column temperature was 40° C. The sample injection volume was 300 μL.

Comparative Example 4

Synthesis of Polymer P-R-1

[Chem. 40]

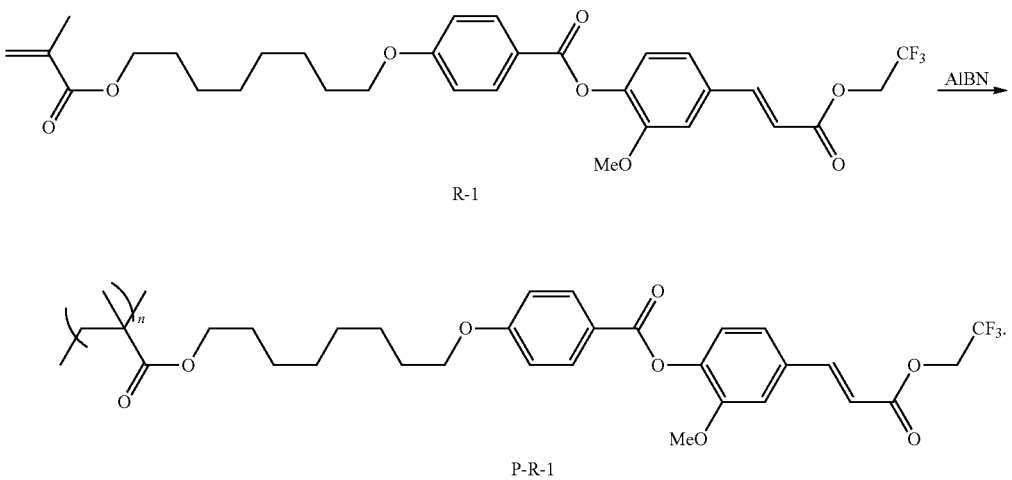

The same procedure as in Example 2 was performed except that 16.5 g of Monomer I-1-1 was replaced with 3 g of Compound R-1 to obtain 1.44 g of Polymer P-R-1. This polymer had a weight average molecular weight of 382,263.

Comparative Example 5

Synthesis of Polymer P-R-2

[Chem. 41]

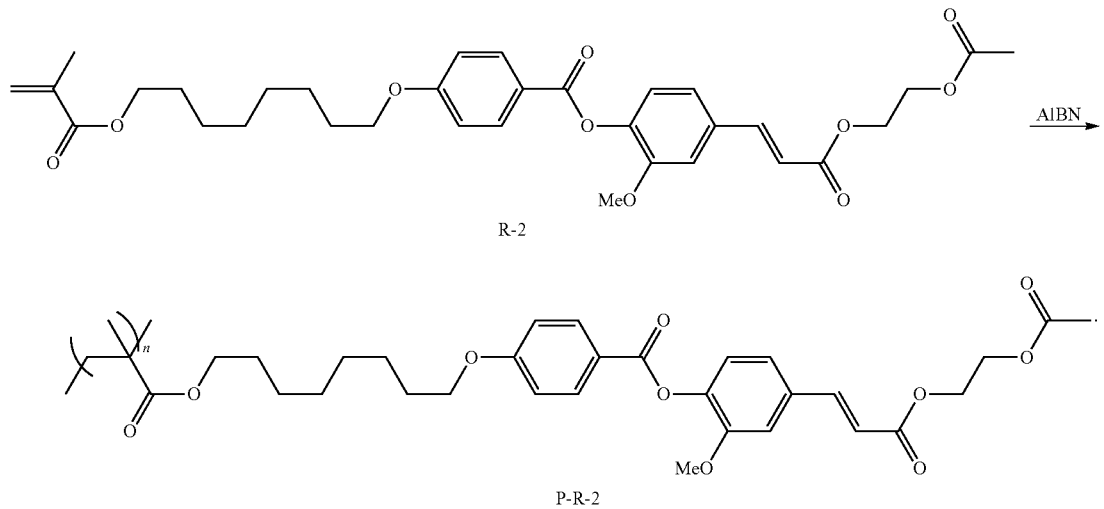

The same procedure as in Example 2 was performed except that 16.5 g of Monomer I-1-1 was replaced with 3 g of Compound R-2 to obtain 1.89 g of Polymer P-R-2. This polymer had a weight average molecular weight of 315,927.

Comparative Example 6

Synthesis of Polymer P-R-3

[Chem. 42]

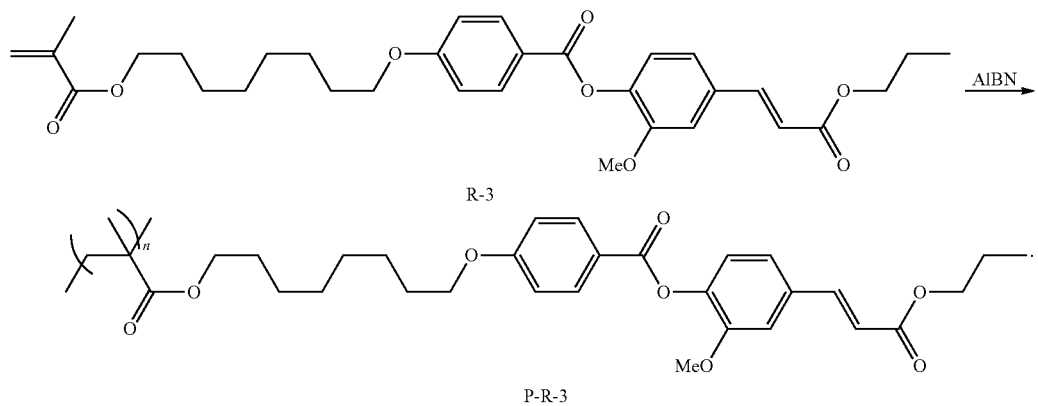

The same procedure as in Example 2 was performed except that 16.5 g of Monomer I-1-1 was replaced with 3 g of Compound R-3 to obtain 1.90 g of Polymer P-R-3, This polymer had a weight average molecular weight of 331,172.

Example 3

Formation of Liquid Crystal Alignment Layer

A mixture of 5 parts of Polymer P-I-1-1 obtained in Example 2, 47.5 parts of N-methylpyrrolidone, and 47.5 parts of 2-butoxyethanol was stirred at room temperature for 10 minutes to uniformly dissolve the polymer. The solution was then applied to glass substrates using a spin coater and was dried at 100° C. for 3 minutes to form a layer on the glass substrates. The resulting layer was found to be smooth by visual inspection.

The resulting layer was exposed to linearly polarized ultraviolet light (wavelength: 313 ms, exposure intensity: 10 mW/cm$^2$) vertically using a polarized light exposure system equipped with a super-high-pressure mercury lamp, a wavelength cut filter, a band-pass filter, and a polarizing filter for 10 seconds to obtain a photoalignment layer exposed to an energy of 100 mJ/cm$^2$. The layer had a thickness of 90 nm.

Comparative Examples 7, 8, and 9

Formation of Liquid Crystal Alignment Layer

Alignment layers were formed on ITO-coated glass substrates by the same procedure as in Example 3 except that Polymer P-I-1-1 obtained in Example 3 was replaced with the polymers obtained in Comparative Examples 4, 5, and 6.

Anchoring Energy Measurement

The anchoring energy of the alignment layers obtained in Example 3 and Comparative Examples 7 to 9 above was measured as follows.

Preparation of Liquid Crystal Composition A

Liquid Crystal Composition A was prepared by mixing the compounds shown in Table 1 below in the proportion shown in the same table. Thermal analysis showed that Liquid Crystal Composition A had a nematic-isotropic liquid phase transition temperature (transparency point) of 85.6° C. Liquid Crystal Composition A also had an extraordinary refractive index $n_e$ of 1.596 at a wavelength of 589 nm, an ordinary refractive index $n_o$ of 1.491 at a wavelength of 589 nm, a dielectric anisotropy of +7.0, and a $K_{22}$ of 7.4 pN.

TABLE 1

| Liquid crystal compound | Content (% by mass) |
|---|---|
| 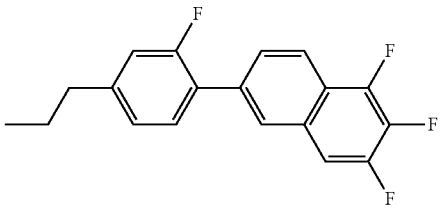 [SMILES: CCCc1ccc(-c2ccc3c(F)c(F)c(F)cc3c2)c(F)c1] | 9 |
| 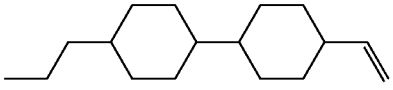 | 37 |
| 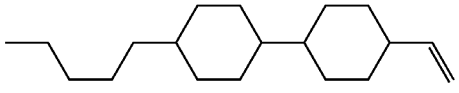 | 2 |
| 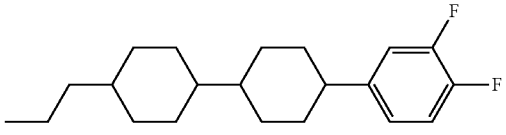 [SMILES: CCCC1CCC(C2CCC(c3ccc(F)c(F)c3)CC2)CC1] | 12 |
| 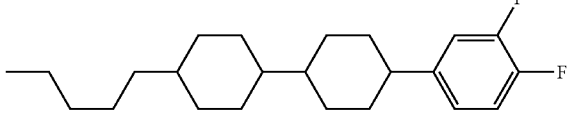 | 12 |
| 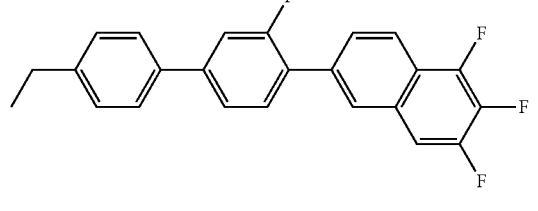 | 4 |
| 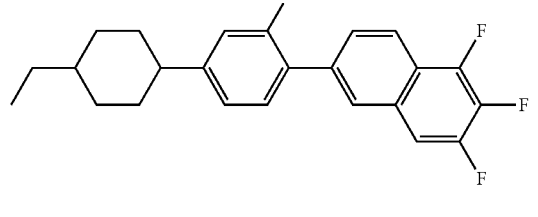 | 6 |

| Liquid crystal compound | Content (% by mass) |
|---|---|
| (structure: propyl-cyclohexyl-difluorophenyl-trifluoronaphthalene) | 13 |
| (structure: propyl-cyclohexyl-CH2-cyclohexyl-cyclohexyl-difluorophenyl) | 5 |

Preparation of Liquid Crystal Composition B

Liquid Crystal Composition B was prepared by adding 0.25% by mass of the compound represented by the following formula to Liquid Crystal Composition A above. The pitch was measured to be 40.40 µm.

[Chem. 43]

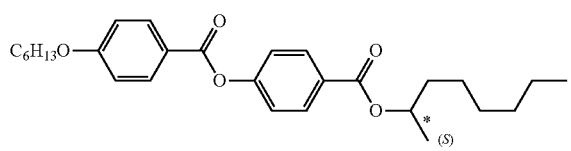

Fabrication of Test Liquid Crystal Cell

Liquid crystal cells were fabricated using the liquid-crystal-alignment-layer-coated glass substrates obtained in Example 3. Specifically, two liquid-crystal-alignment-layer-coated glass substrates were placed such that the liquid crystal alignment layers thereof faced each other and that the directions in which they were exposed to linearly polarized light were antiparallel. The peripheries of the two substrates were then bonded together with a sealant such that a predetermined gap (10 µm) was maintained therebetween. The cell gap defined by the surfaces of the liquid crystal alignment layers and the sealant was filled with Liquid Crystal Composition A or B immediately above the transparency point, followed by cooling to room temperature to obtain a liquid crystal cell, The resulting liquid crystal cells were used as test devices. The anchoring energy was measured to be 250 µJ/m² by the following procedure.

Azimuthal Anchoring Energy Measurement

The liquid crystal cells were tested for the azimuthal anchoring energy at the interfaces between the surfaces of the liquid crystal alignment layers and the liquid crystal layer by the following torque balance method (as reported in The Japanese Liquid Crystal Society Conference Proceedings (2001), pp. 251 and 252).

A liquid crystal cell was first vacuum-filled with Liquid Crystal Composition A, was heated at 92° C. for 2 minutes, and was cooled to room temperature.

An optical measurement system (OMS-DI4RD, Chuo Precision Industrial Co., Ltd.) equipped with a white light source, a polarizer (entrance polarizer), an analyzer (exit polarizer), and a detector was then provided. The liquid crystal cell was placed between the polarizer and the analyzer. The intensity of transmitted light was detected with the detector while the polarizer and the analyzer were rotated relative to each other. The twist angle $\Phi_1$ was determined as the angle of rotation between the polarizer and the analyzer at which the detected light intensity was minimized (extinction direction). The twist angle $\Phi_1$ was 1.12°.

Another liquid crystal cell was then vacuum-filled with Liquid Crystal Composition B instead of Liquid Crystal Composition A and was similarly heated and cooled, and the twist angle of the liquid crystal cell was determined. The twist angle $\Phi_2$ of the liquid crystal cell filled with Liquid Crystal Composition A was 1.64°.

The azimuthal anchoring energy A was calculated by equation (1) below.

$$A = 2K_{22}(2\pi d/p - \Phi_2)/d \cdot \sin(\Phi_2 - \Phi_1) \tag{1}$$

where $K_{22}$ is the twist elastic modulus of the liquid crystal, d is the cell gap, and p is the helical pitch of the chiral liquid crystal.

The alignment layers obtained in Comparative Examples 7 to 9 were also tested for anchoring energy as in Example 3. The anchoring energies of the alignment layers obtained in Comparative Examples 7 to 3 were 40 µJ/m², 100 µJ/m², and 60 µJ/m², respectively.

The above results demonstrate that the compound having at least one cyano group at an end of the molecule (cinnamic acid derivative) in Example 1 and the polymer thereof can be used to form a liquid crystal alignment layer having a sufficient anchoring energy with less linearly polarized light for exposure. Such a liquid crystal alignment layer is effective in controlling the orientation and pretilt angle of liquid crystals. In contrast, the liquid crystal alignment layers obtained in the Comparative Examples where the compounds of Comparative Examples 1 to 3, which contained no cyano group, and the polymers thereof were used had lower anchoring energies than those obtained in the Examples.

INDUSTRIAL APPLICABILITY

The present invention can provide a liquid crystal alignment layer to which alignment properties can be efficiently induced with less polarized light for exposure during manufacture, that is effective in controlling the orientation and pretilt angle of liquid crystals, and that has a high voltage holding ratio (VHR). The present invention can also provide a polymer for such a liquid crystal alignment layer, a compound that forms such a polymer, a liquid crystal display device including such a liquid crystal alignment layer, and an optically anisotropic material formed using such a polymer. Such an optically anisotropic material is useful for the manufacture of an optically anisotropic film that can be used for optical compensation or Other applications.

The invention claimed is:

1. A compound represented by general formula (I):

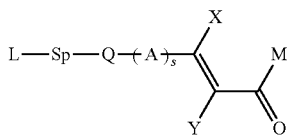

(I)

wherein
L is a polymerizable group;
Sp is a spacer unit comprising methylene;
Q is a direct bond, —O—, —CO—O—, or —O—CO—;
A comprises a group selected from the group consisting of trans-1,4-cyclohexylene (wherein one or more non-adjacent methylene groups present in this group are optionally replaced with —O—, —NH—, or —S—), 1,4-phenylene (wherein one or more —CH═groups present in this group are optionally replaced with—N═), 1,4-cyclohexenylene, 2,5-thiophenylene, 2,5-furanylene, 1,4-bicyclo[2,2,2]octylene, naphdialene-1,4-diyl, naphthalene-2,6-diyl, decahydronaphthalene-2,6-diyl, and 1,2,3,4-tetrahydronaphthalene-2,6-diyi, wherein the groups are unsubstituted, or one or more hydrogen atoms present therein are optionally replaced with fluorine, chlorine, cyano, methyl, or methoxy;
s is an integer of 1 to 4, wherein if s is 2 to 4, each A may be the same or different;
X and Y are each independently hydrogen, fluorine, chlorine, cyano, or an alkyl group of 1 to 20 carbon atoms, wherein any hydrogen atom present in the alkyl group is optionally replaced with fluorine, and if one or more non-adjacent methylene groups are present in the alkyl group, the one or more non-adjacent methylene groups are optionally replaced with —O—, —CO—O—, —O—CO—, and/or —CH═CH—, and
M is any of general. formulas (IIa), (IIb), and (IIc):

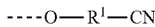

(IIa)

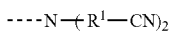

(IIb)

(IIc)

wherein
the dashed line is a linkage to the carbon atom;
$R^1$ is an alkylene group of 1 to 30 carbon atoms, wherein each $R^1$, if present, may be the same or different;
$R^2$ is hydrogen or an alkyl group of 1 to 30 carbon atoms; and
if one or more non-adjacent methylene groups are present in $R^1$ and $R^2$, the one or more non-adjacent methylene groups are optionally replaced with —O—, —CO—, —CO—O—, —CO—, —CO—NH—, —NH—CO—, —NCH₃—, —CH═CH—, —CF═CF—, and/or —C≡C—, and any hydrogen atom present in $R^1$ and $R^2$ is optionally replaced with an alkyl group of 1 to 20 carbon atoms, cyano, or halogen.

2. The compound according to claim 1, wherein $R^1$ in general formulas (IIa), (IIb), and (IIc) is represented by general formula (IId):

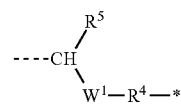

(IId)

wherein
the dashed line is a linkage to the oxygen or nitrogen atom, and * is a linkage to the cyano group;
$W^1$ is methylene (wherein any hydrogen atom present in this group is optionally replaced with an alkyl group of 1 to 5 carbon atoms), —CO—O—, or —CO—NH—;
$R^4$ is an alkylene group of 1 to 20 carbon atoms, wherein if one or more non-adjacent methylene groups are present in the alkylene group, the one or more non-adjacent methylene groups are optionally replaced with —O—, —CO—, —CO—O—, —O—CO—, —CO—NH—, —NH—CO—, or —NCH₃—; and
$R^5$ is hydrogen or an alkyl group of 1 to 5 carbon atoms, wherein any hydrogen atom present in the alkyl group is optionally replaced with fluorine or chlorine.

3. The compound according to claim 1, wherein A in general formula (I) is 1,4-phenyiene wherein one or more hydrogen atoms present in the 1,4-phenylene group are optionally replaced with fluorine, chlorine, methyl, or methoxy.

4. The compound according, to claim 1, wherein X and Y in general formula (I) are hydrogen.

5. The compound according to claim 1 wherein L in general formula (I) is any polymerizable group selected from the group consisting of polymerizable groups represented by general formulas (III-1) to (III-10):

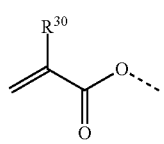

(III-1)

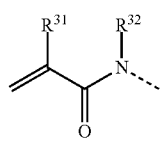

(III-2)

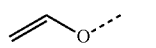

(III-3)

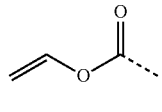

(III-4)

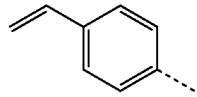

(III-5)

-continued (III-6)

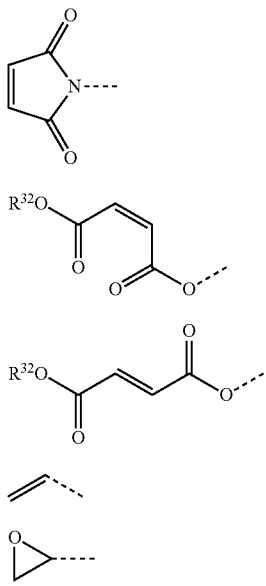

(III-7)

(III-8)

(III-9)

(III-10)

wherein the dashed line is a linkage to Sp; $R^{30}$ is hydrogen, fluorine, chlorine, an alkyl group of 1 to 4 carbon atoms, phenyl, or phenoxy; $R^{31}$ is hydrogen, chlorine, methyl, or phenyl; and $R^{32}$ is each independently hydrogen or an alkyl group of 1 to 5 carbon atoms.

6. The compound according to claim 1, wherein L in general formula (I) is any of polymerizable groups represented by general formulas (III-1) (III-2) and (III-6):

(III-1)

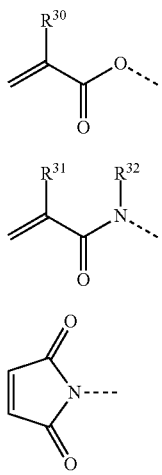

(III-2)

(III-6)

wherein the dashed line is a linkage to Sp; $R^{30}$ and $R^{31}$ are each independently hydrogen or methyl; and $R^{32}$ is hydrogen or an alkyl group of 1 to 5 carbon atoms.

7. The compound according to claim 1, wherein -(A)$_s$- in general formula (I) is represented by general formula (IVa):

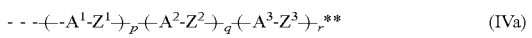 (IVa)

wherein
the dashed line is a linkage to Q. and ** is a linkage to the carbon atom;
$A^1$, $A^2$, and $A^3$ are each independently a group selected from the group consisting of trans-1,4-cyclohexylene (wherein one or more non-adjacent methylene groups present in this group are optionally replaced with —O—, —NH—, or —S—), ,4-phenylene (wherein one or more —CH═groups present in this group are optionally replaced with 1,4-cyclohexenylene, 2,5-thiophenylene, 2,5-aranylene, 1,4-bicyclo[2,2,2]octylene, naphthalene-1,4-diyl, naphthalene-2,6-diyl, decahydronaphthalene-2,6-diyl, and 1,2,3,4-tetrahydronaphthalene-2,6-diyl, wherein the groups are unsubstituted, or one or more hydrogen atoms present therein are optionally replaced with fluorine, chlorine, cyano, methyl, or methoxy;

$Z^1$, $Z^2$, and $Z^3$ are each independently a single bond, an alkylene group of 1 to 20 carbon atoms, —OCH$_2$—, —CH$_2$O—, —CO —O—, —O—, —CO—, —CH═CH—, —CF═CF—, -CF$_2$O—, -OCF$_2$—, —CF$_2$CF$_2$—, or —C≡C— wherein if one or more non-adjacent methylene groups are present in these substituents, the one or more non-adjacent methylene groups are each independently optionally replaced with —O—, —CO—, —CO —O—, —O—CO—, —Si (CH$_3$)$_2$—O—Si(CH$_3$)$_2$—, —NR$^6$—, —NR$^6$—CO—, —CO—NR$^6$, —NR$^6$—CO—O—, —O—CO—NR$^6$—, —NR$^6$—CO—NR$^6$—, —CH═CH—, —C≡C—, or —O—CO—O—, wherein $R^6$ is each independently hydrogen or an alkyl group of 1 to 5 carbon atoms; and p, q, and r are each an integer of 0 to 4, wherein p+q+r=s.

8. The compound according to claim 7, wherein, in general formula (IVa), $A^2$ is any of trans-1 ,4-cyclohexylene, 2,6-naphthylene, pyridine-2,5-diyl, pyrimidine-2,5-diyl, and 1,4-phenylene, wherein one or more hydrogen atoms present in the groups are optionally replaced with fluorine, chlorine, methyl, or methoxy;

$Z^2$ is any of a single bond, an alkylene group of 1 to 20 carbon atoms, —OCH$_2$—, —CH$_2$O—, —CO—O—, —O—CO—, —CH═CH—, and —C≡—, wherein if one or more non-adjacent methylene groups are present in the groups, the one or more non-adjacent methylene groups are each independently optionally replaced with —O—, —CO—, —CO—O—, —O—CO—, —CH═CH—, or —C≡C—; and q is 1.

9. The compound according to claim 7, wherein $A^2$ in general formula (IVa) is 1,4-phenylene, wherein one or more hydrogen atoms present in the 1,4-phenylene group are optionally replaced with fluorine, chlorine, methyl, or methoxy.

10. A polymer obtained by polymerization of a composition comprising the compound according to claim 1, the polymer comprising structural units represented by general formula (PI):

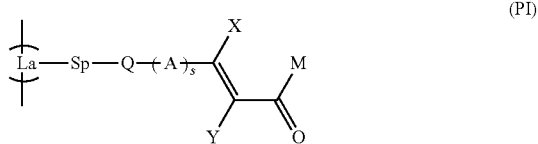 (PI)

wherein La is a group derived from L, and Sp, Q, A, X. Y M, and s are as defined in general formula (I).

11. A liquid crystal alignment layer for use in a vertically aligned liquid crystal display device, the liquid crystal alignment layer comprising a cured product of the polymer according to claim 10.

12. A vertically aligned liquid crystal display device comprising t le liquid crystal alignment layer according to claim 11.

13. A liquid crystal alignment layer for use in a horizontally aligned liquid crystal display device, the liquid crystal alignment layer comprising a cured product of the polymer according to claim 10.

14. A horizontally aligned liquid crystal display device comprising the liquid crystal alignment layer according to claim 13.

15. An optically anisotropic material uprising a polymer of a polymerizable liquid crystal composition, wherein polymerizable liquid crystal molecules the polymerizable liquid crystal composition are aligned by a liquid crystal alignment layer comprising a cured product of the polymer according to claim 10.

* * * * *